United States Patent [19]

Weinberger

[11] Patent Number: 5,707,332

[45] Date of Patent: Jan. 13, 1998

[54] APPARATUS AND METHOD TO REDUCE RESTENOSIS AFTER ARTERIAL INTERVENTION

[75] Inventor: Judah Z. Weinberger, Teaneck, N.J.

[73] Assignee: The Trustees of Columbia University in the City of New York, New York, N.Y.

[21] Appl. No.: 565,093

[22] Filed: Nov. 30, 1995

Related U.S. Application Data

[63] Continuation-in-part of Ser. No. 184,380, Jan. 21, 1994, Pat. No. 5,503,613.

[51] Int. Cl.⁶ .................................................. A61N 5/00
[52] U.S. Cl. .................................................. 600/3
[58] Field of Search ........................ 600/1–8; 128/656–59

[56] References Cited

U.S. PATENT DOCUMENTS

| | | | |
|---|---|---|---|
| 3,324,847 | 6/1967 | Zoumboulis | 128/1.2 |
| 3,811,426 | 5/1974 | Culver et al. | 128/1.2 |
| 3,927,325 | 12/1975 | Hungate et al. | 250/435 |
| 4,770,653 | 9/1988 | Shturman | 604/21 |
| 5,213,561 | 5/1993 | Weinstein et al. | 600/7 |
| 5,302,168 | 4/1994 | Hess | 600/3 |
| 5,411,466 | 5/1995 | Hess | 600/3 |
| 5,540,659 | 7/1996 | Teirstein | 604/104 |
| 5,616,114 | 4/1997 | Thorton et al. | |

FOREIGN PATENT DOCUMENTS

| | | | |
|---|---|---|---|
| 9102312.2 | 8/1992 | Germany | A61N 36/04 |
| 9617654 | 6/1996 | WIPO | A61N 5/00 |

OTHER PUBLICATIONS

Joseph Wiedermann, Jeffrey Leavy, Howard Amols, Allan Schwartz, Shunichi Homma, Charles Marboe, Juday Weinberger; "Effects of High Dose Intracoronary Irradiation on Vasomotor Function and Smooth Muschle Histopathology". AHA, Oct. 1992.

Joseph G. Wiedermann, Charles Marboe, Howard Amols, Allan Schwartz, Judah Weinberger; "Intraccoronary Irradiation Markedly Reduces Restenosis After Balloon Angioplasty in a Porcine Model". AHA, Oct. 1993.

Primary Examiner—John P. Lacyk
Attorney, Agent, or Firm—John P. White

[57] ABSTRACT

An apparatus guided by a guidewire within a patient's artery for reducing restenosis after arterial intervention in the patient's artery. A radiation dose delivery wire with a radiation source encapsulated within its distal end is inserted into a blind lumen in a balloon catheter to deliver radiation to a target area of the patient's artery.

9 Claims, 14 Drawing Sheets

APPARATUS AND METHOD TO REDUCE RESTENOSIS AFTER ARTERIAL INTERVENTION

This application is a continuation-in-part of application Ser. No. 08/184,380, filed Jan. 21, 1994 now U.S. Pat. No. 5,503,613.

BACKGROUND OF THE INVENTION

The present invention relates to an apparatus and a method to reduce restenosis after arterial intervention.

Within this application several publications are referenced by Arabic numerals within parentheses. Full citations for these and other references may be found at the end of the specification immediately preceding the claims. The disclosures of all of these publications in their entireties are hereby incorporated by reference into this application in order to more fully describe the state of the art to which this invention pertains.

Percutaneous transluminal coronary angioplasty ("PCTA") is commonly used in the treatment of coronary artery obstruction, with over 400,000 procedures performed annually. The process involves the insertion of balloon catheters through the femoral artery to the targeted coronary artery. Injection of radio-opaque contrast into the proximal coronary artery allows fluoroscopic localization of stenosed coronary segments. Balloon catheters are advanced to the site of stenosis over extremely thin guide wires to position the catheter at the point of occlusion. The distal end of the catheter contains a balloon which is inflated for 2-4 minutes to the full diameter of the occluded artery, decreasing the blockage and improving blood flow.

Approximately 40% of patients undergoing this procedure have angiographic evidence of restenosis by 12 months. The biological processes responsible for restenosis are not fully understood, but appear to result from abnormal proliferation of the 'insulted' smooth muscle cells and neointima formation in the segment of treated artery (6). Although coronary artery blockage is a non-malignant disease, it has been suggested that treatment of the internal vessel walls with ionizing radiation could inhibit cell growth, and delay or even prevent restenosis (4, 7, 10–13).

As stated above, restenosis after arterial intervention in general, PTCA in particular, seem to be primarily due to medial smooth muscle cell proliferation. Conventional PTCA is performed using a balloon catheter such an over-the-wire type catheter manufactured, for example, by Scimed Life Systems, Inc, of Maple Grove, Minnesota or a mono-rail type catheter manufactured, for example, by Advanced Cardiovascular Systems, Inc, of Temecula, Calif. FIG. 1 depicts such a conventional over-the-wire balloon catheter 1. The conventional balloon catheter 1 is utilized in an angioplasty procedure as follows. A conventional guidewire 2 is inserted into the patient's artery until the distal end of the guidewire 2 is past a target area (not shown) of the artery (not shown) where there is a buildup of material. The conventional balloon catheter 1 has a lumen 3 running therethrough. The guidewire 2 is inserted into the distal end of the balloon catheter 1 and the balloon catheter 1 is advanced over the guidewire until the balloon section 1a of the balloon catheter 1 is adjacent the buildup of material. The balloon section 1a is then inflated by an inflation means (not show) connected to an inflation port 1b to clear the artery. Finally, the balloon section 1a is deflated, the balloon catheter 1 is pulled back up the guidewire and removed and the guidewire is likewise removed from the patient's artery.

Current technology contemplates two distinct design classes for devices for the prevention of restenosis after arterial interventions. The first design class, an arterial stent type device, is designed for long term deployment within the artery. Such a stent, if designed to emit radiation, would be in place long after the time necessary for the prevention of smooth muscle cell proliferation at the arterial site. U.S. Pat. No. 5,059,166 to Fischell describes such a long term stent.

The second design class for restenosis preventing devices contemplates the delivery of unspecified doses of radiation via radioactive catheters and guidewires. These devices utilize a movable, flexible radiation shield. However, it is questionable whether such a radiation shield could be constructed given the thickness of material required to shield the radiation source and the flexibility required to allow delivery of the radiation source and shield to the coronary site. U.S. Pat. No. 5,213,561 to Weinstein relates to a device of this class.

In addition, neither class of devices addresses the need to isolate the radioactive source from contact with the patient's body fluids.

SUMMARY OF THE INVENTION

It is an object of the present invention to provide an arrangement for reducing restenosis after arterial or vascular intervention in a patient. Such intervention includes, but is not limited to, balloon angioplasty, atherectomy, stent placement, arterial grafts, and arteriovenous fistula.

Moreover, it is noted that long term hemodialysis therapy is complicated by thrombosis of both hemodialysis grafts and native shunts. Late graft failure (after about 6 weeks) is commonly associated with anatomic stenosis at the venous anastomosis, within the graft, or more proximally in the central venous system. Irradiation of the proliferative tissue from an intravascular source will inhibit the development of shunt outflow stenosis and thus decrease the incidence of thrombosis from the ensuing low flow state. Any proliferative tissue at the site of a vascular graft would also be amenable to this treatment.

It is a further object of the present invention to provide an arrangement for reducing restenosis after vascular intervention in the patient by delivering a precise dosage of radiation to the patient's artery at a target area.

It is a further object of the present invention to provide an arrangement for reducing restenosis after vascular intervention in the patient by delivering precise radioactive dosage to the patient's artery at a target area while eliminating contact between the radioactive source and the patient's body fluids.

It is a further object of the present invention to provide an arrangement for reducing restenosis after vascular intervention in the patient by delivering a precise radioactive dosage to the patient's artery at a target area while shielding a doctor and other staff from over-exposure to radiation.

According to one aspect of the present invention, an apparatus guided by a guidewire within a patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation delivery wire into its proximal end.

According to another aspect of the present invention, an apparatus inserted into a sheath in a patent's artery and guided by a guidewire within the patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation dose delivery wire into its proximal end, said balloon catheter being adapted to be inserted into said sheath.

According to another aspect of the present invention, an apparatus guided by a guidewire within a patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending partially through said balloon catheter, said blind lumen being adapted to accept said radiation dose delivery wire into its proximal end, said guidewire lumen having an entry port located at a distal end of said balloon catheter and an exit port located upon a circumferential surface of said balloon catheter.

According to another aspect of the present invention, an apparatus for reducing restenosis after arterial intervention in a patient's artery is provided, comprising a guidewire for insertion into the patient's artery at least as far as a target area of the artery, a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation delivery wire into its proximal end.

According to another aspect of the present invention, an apparatus guided by a guidewire within a patient's artery for reducing restenosis after arterial intervention in the patient's artery is provided, comprising a radiation dose delivery wire with a radiation source encapsulated within its distal end, and a catheter with a blind lumen sealed at its distal end and a guidewire lumen extending therethrough to accept said guidewire, said blind lumen being adapted to accept said radiation delivery wire into its proximal end.

According to another aspect of the present invention, an apparatus to be inserted into a catheter for reducing restenosis after arterial intervention in a patient's artery is provided, comprising a radiation dose delivery wire with a radiation source encapsulated within its distal end, and a blind lumen open at its proximal end and sealed at its distal end, said blind lumen being adapted to accept said radiation dose delivery wire into its proximal end and to be inserted into said catheter.

According to another aspect of the present invention, a method of reducing restenosis after arterial intervention in a patient's artery is provided, comprising inserting a guidewire into the patient's artery until a distal end of the guidewire is at least as far into the artery as a predetermined section of the artery, inserting the guidewire into a guidewire lumen of a balloon catheter with a blind lumen, inserting the balloon catheter with the blind lumen into the patient's artery at least as far as the predetermined section of the artery, inserting a radiation dose delivery wire into said blind lumen in said balloon catheter, moving said radiation dose delivery wire a predetermined distance into the blind lumen of the balloon catheter for a predetermined period of time, and removing said radiation dose delivery wire from said blind lumen of said balloon catheter after said predetermined period of time.

According to another aspect of the instant invention an apparatus for use with a guidewire for reducing restenosis after arterial intervention in a patient's artery is provided, comprising a balloon catheter with a guidewire lumen extending therethrough adapted to accept a guidewire for guiding the balloon catheter in the patient's artery, said balloon catheter having a radiation producing coating on an internal surface.

The radiation producing coating may include a material selected from the group consisting of Al-26, Sn-123, K-40, Sr-89, Y-91, Ir-192, Cd-115, P-32, Rb-86, I-125, Pd-103, and Sr-90, or any other material selected from Table 2, for example.

Regarding Tables 2–4, it is noted that the legend "A" refers to atomic mass, the half-life is given in years, days, hours, and minutes, where appropriate, a "Rad. Type" (radiation type) B+ indicates emission of a positron particle, B– indicates the emission of a beta particle, and G indicates the emission of a gamma photon.

The radiation producing coating may comprise a lacquer, a glue, an acrylic, or a vinyl.

The balloon portion of the catheter may be formed of a plastic material such as polyethylene, PET, and nylon.

According to another aspect of the instant invention an apparatus for use with a guidewire for reducing restenosis after arterial intervention in a patient's artery is provided, comprising a balloon catheter with a guidewire lumen extending therethrough adapted to accept a guidewire for guiding the balloon catheter in the patient's artery, said balloon catheter having a radiation producing coating on an exterior surface.

The radiation producing coating may include a material selected from the group consisting of Al-26, Sn-123, K-40, Sr-89, Y-91, Ir-192, Cd-115, P-32, Rb-86, I-125, Pd-103, and Sr-90, or any other material selected from Table 2, for example.

The radiation producing coating may comprise a lacquer, a glue, an acrylic, or a vinyl.

The balloon catheter may be formed of a plastic material chosen from the group consisting of polyethylene, PET, and nylon.

According to another aspect of the instant invention an apparatus for use with a guidewire for reducing restenosis after arterial intervention in a patient's artery is provided, comprising a balloon catheter with a guidewire lumen extending therethrough adapted to accept a guidewire for guiding the balloon catheter in the patient's artery, said balloon catheter being formed of a flexible material including a radiation producing source.

The flexible material may be formed of a plastic material such as polyethylene, PET, and nylon.

The plastic material may be doped with said radiation producing source.

The radiation producing source may be chemically bonded to said plastic material by a covalent bond.

The radiation producing source may be bonded to said plastic material by an ionic bond.

The radiation producing source may be bonded to said plastic material by a biotin-avidin link.

The radiation producing source may be bonded to said plastic material by coextrusion.

According to another aspect of the instant invention a method for reducing restenosis after arterial intervention in a patient's artery is provided, comprising inserting a balloon catheter with a fluid delivery port connected thereto into the patient's artery and inserting a radioactive fluid into the balloon catheter through the fluid delivery port.

The radioactive fluid may be selected from the group consisting of fluids containing Cu-61, Se-73, Co-55, Sc-44, Sr-75, Kr-77, Ga-68, In-110, Br-76, Ga-66, Ga-72, Sb-122, Na-24, Si-31, Ge-77, Ho-166, Re-188, Bi-212, Y-90, K-42, Ir-192, I-125, Pd-103, Sr-90, and radioactive sodium-chloride, or any other chemical compound formulated from the isotopes given in Table 3, for example.

According to another aspect of the instant invention an apparatus guided by a guidewire within a patient's artery for receiving a radiation dose delivery wire with a radiation source encapsulated within its distal end and for reducing restenosis after arterial intervention in the patient's artery is provided, comprising a balloon catheter with a blind lumen sealed at its distal end and a guidewire lumen extending therethrough to accept said guidewire, said blind lumen being adapted to accept said radiation delivery wire into its proximal end.

These and other advantages will become apparent from the detailed description, accompanying the claims and attached drawing figures.

DETAILED DESCRIPTION OF THE DRAWINGS

Figure 1:
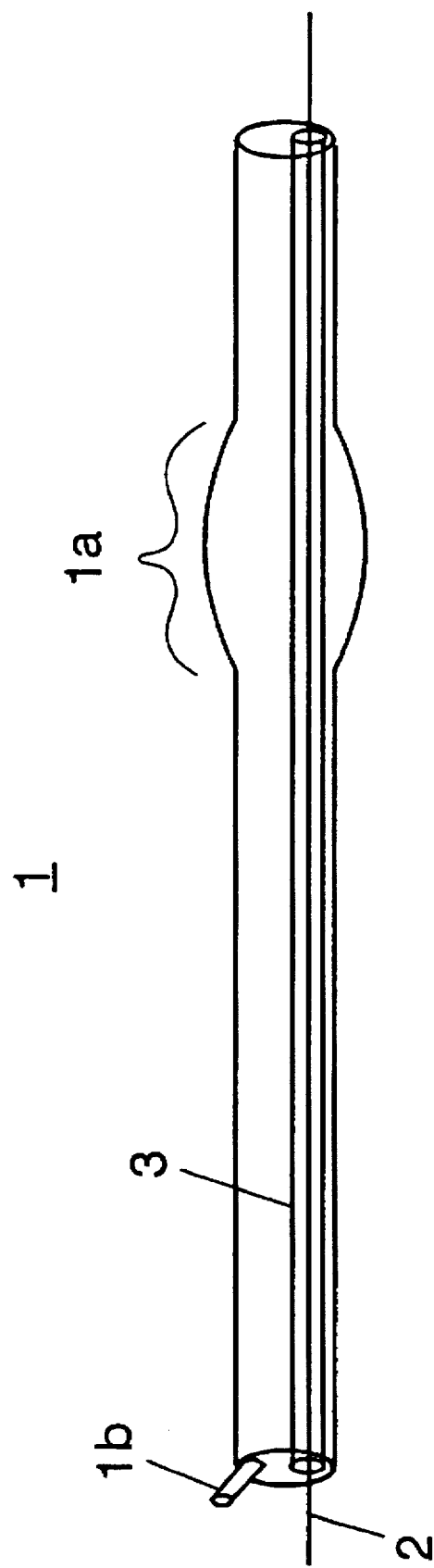
FIG. 1. shows the construction of a conventional over-the-rail type balloon catheter.

According to one aspect of the present invention, an apparatus guided by a guidewire within a patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation delivery wire into its proximal end.

The apparatus may further comprise means for providing a liquid-tight seal between the radiation dose delivery wire and the proximal end of the blind lumen.

The means for providing a liquid-tight seal may comprise a liquid-tight radiation delivery wire port connected to the proximal end of the blind lumen, whereby a liquid-tight seal is effectuated between the proximal end of the blind lumen and the radiation dose delivery wire. Alternatively, the means for providing a liquid-tight seal may effectuate a liquid-tight seal between the proximal end of the blind lumen and an afterloader which drives the radiation dose delivery wire.

The radiation source may be a pellet, a wire, or an encapsulated radiation source, such as a paste of Ir-192, I-125, or Pd-103. Alternatively, the radiation source may be a γ-radiation emitting isotope. The length of the radiation source is determined by the length of the segment of diseased vessel, that is, the segment of vessel which is to receive a dose of radiation. The radiation source may be 0.5 to 5 cm in length and it may comprise a plurality of radioactive pellets forming a linear array.

The apparatus may further comprise means for moving the distal end of said radiation dose delivery wire to a predetermined position within said blind lumen for a predetermined period of time. The means for moving may be a computer controlled afterloader. The computer controlled afterloader may calculate said predetermined position and said predetermined time.

The computer controlled afterloader may further calculate said predetermined position and said predetermined time based upon a plurality of input variables including a half-life of the radiation source, an activity level of the radiation source, an angiograghic or ultrasound determined diameter of said artery, and a desired radiation dosage to be delivered to the artery at the predetermined position. A user may input a plurality of values each representing respective ones of the plurality of input variables to the computer controlled afterloader. The computer controlled afterloader may oscillate said distal end of said radiation dose delivery wire back and forth in the area of the predetermined position for a predetermined period of time.

An outer diameter of the guidewire and an outer diameter of the radiation dose delivery wire may be substantially equal to 0.014 inch. The radiation source may have a radioactivity of less than about 10 Curies.

The apparatus may further comprise a radiation blocking shield movable between the radiation source within the patient's artery and a user of the apparatus. The radiation blocking shield may be concrete or lead.

According to another aspect of the present invention, an apparatus inserted into a sheath in a patient's artery and guided by a guidewire within the patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation dose delivery wire into its proximal end, said balloon catheter being adapted to be inserted into said sheath.

The apparatus may further comprise means for providing a liquid-tight seal between the radiation dose delivery wire and the proximal end of the blind lumen.

The apparatus may further comprise means for maintaining an extended coaxial relationship between the proximal end of said sheath and the proximal end of said blind lumen.

According to another aspect of the present invention, an apparatus guided by a guidewire within a patient's artery for reducing restenosis after arterial intervention in the patient's artery is provided, comprising a radiation dose delivery wire with a radiation source encapsulated within its distal end, and a balloon catheter with a blind lumen sealed at its distal end and a guidewire lumen extending partially through said balloon catheter, said blind lumen being adapted to accept said radiation dose delivery wire into its proximal end, said guidewire lumen having an entry port located at a distal end of said balloon catheter and an exit port located upon a circumferential surface of said balloon catheter.

According to another aspect of the present invention, an apparatus for reducing restenosis after arterial intervention in a patient's artery is provided, comprising a guidewire for insertion into the patient's artery at least as far as a target area of the artery, a radiation dose delivery wire with a radiation source encapsulated within its distal end, and a balloon catheter with a blind lumen sealed at its distal end and a guidewire lumen extending therethrough to accept said guidewire, said blind lumen being adapted to accept said radiation delivery wire into its proximal end.

According to another aspect of the present invention, an apparatus guided by a guidewire within a patient's artery for reducing restenosis after arterial intervention in the patient's artery is provided, comprising a radiation dose delivery wire with a radiation source encapsulated within its distal end, and a catheter with a blind lumen sealed at its distal end and a guidewire lumen extending therethrough to accept said guidewire, said blind lumen being adapted to accept said radiation delivery wire into its proximal end.

The apparatus may further comprise means for providing a liquid-tight seal between the radiation dose delivery wire and the proximal end of the blind lumen.

According to another aspect of the present invention, an apparatus to be inserted into a catheter for reducing restenosis after arterial intervention in a patient's artery is provided, comprising a radiation dose delivery wire with a radiation source encapsulated within its distal end, and a blind lumen open at its proximal end and sealed at its distal end, said blind lumen being adapted to accept said radiation dose delivery wire into its proximal end and to be inserted into said catheter.

The apparatus may further comprise means for providing a liquid-tight seal between the radiation dose delivery wire and the proximal end of the blind lumen.

According to another aspect of the present invention, a method of reducing restenosis after arterial intervention in a patient's artery is provided, comprising inserting a guidewire into the patient's artery until a distal end of the guidewire is at least as far into the artery as a predetermined section of the artery, inserting the guidewire into a guidewire lumen of a balloon catheter with a blind lumen, inserting the balloon catheter with the blind lumen into the patient's artery at least as far as the predetermined section of the artery, inserting a radiation dose delivery wire into said blind lumen in said balloon catheter, moving said radiation dose delivery wire a predetermined distance into the blind lumen of the balloon catheter for a predetermined period of time, and removing said radiation dose delivery wire from said blind lumen of said balloon catheter after said predetermined period of time.

The method of moving said radiation dose delivery wire a predetermined distance into the blind lumen of the balloon catheter for a predetermined period of time may result in the distal end of the radiation dose delivery wire being adjacent said predetermined section of artery.

The method of moving said radiation dose delivery wire a predetermined distance into the blind lumen of the balloon catheter for a predetermined period of time may further comprise determining where the predetermined section of artery is, determining a diameter of said predetermined section of artery, and determining a desired radiation dosage to be delivered to the predetermined section of artery. The diameter may be determined by an angiograghic or ultrasound procedure.

The method of moving said radiation dose delivery wire a predetermined distance into the blind lumen of the balloon catheter for a predetermined period of time may further comprise oscillating said radiation dose delivery wire back and forth when said distal end of radiation dose delivery wire is substantially adjacent said predetermined section of artery.

According to another aspect of the instant invention an apparatus for use with a guidewire for reducing restenosis after arterial intervention in a patient's artery is provided, comprising a balloon catheter with a guidewire lumen extending therethrough adapted to accept a guidewire for guiding the balloon catheter in the patient's artery, said balloon catheter having a radiation producing coating on an internal surface.

The radiation producing coating may include a material selected from the group consisting of Al-26, Sn-123, K-40, Sr-89, Y-91, Ir-192, Cd-115, P-32, Rb-86, I-125, Pd-103, and St-90, or any other material selected from Table 2, for example.

The radiation producing coating may comprise a lacquer, a glue, an acrylic, or a vinyl.

The balloon portion of the catheter may be formed of a plastic material selected from the group consisting of polyethylene, PET, and nylon.

According to another aspect of the instant invention an apparatus for use with a guidewire for reducing restenosis after arterial intervention in a patient's artery is provided, comprising a balloon catheter with a guidewire lumen extending therethrough adapted to accept a guidewire for guiding the balloon catheter in the patient's artery, said balloon catheter having a radiation producing coating on an exterior surface.

The radiation producing coating may include a material selected from the group consisting of Al-26, Sn-123, K-40, Sr-89, Y-91, Ir-192, Cd-115, P-32, Rb-86, I-125, Pd-103, and Sr-90, or any other material selected from Table 2, for example.

The radiation producing coating may comprise a lacquer, a glue, an acrylic, or a vinyl.

The balloon portion of the catheter may be formed of a plastic material selected from the group consisting of polyethylene, PET, and nylon.

According to another aspect of the instant invention an apparatus for use with a guidewire for reducing restenosis after arterial intervention in a patient's artery is provided, comprising a balloon catheter with a guidewire lumen extending therethrough adapted to accept a guidewire for guiding the balloon catheter in the patient's artery, said balloon catheter being formed of a flexible material including a radiation producing source.

The flexible material may be formed of a plastic material selected from the group consisting of polyethylene, PET, and nylon.

The plastic material may be doped with said radiation producing source.

The radiation producing source may be chemically bonded to said plastic material by a covalent bond.

The radiation producing source may be bonded to said plastic material by an ionic bond.

The radiation producing source may be bonded to said plastic material by a biotin-avidin link.

The radiation producing source may be bonded to said plastic material by coextrusion.

According to another aspect of the instant invention a method for reducing restenosis after arterial intervention in a patient's artery is provided, comprising inserting a balloon catheter with a fluid delivery port connected thereto into the patient's artery and inserting a radioactive fluid into the balloon catheter through the fluid delivery port.

The radioactive fluid may be selected from the group consisting of fluids containing Cu-61, Se-73, Co-55, Sc-44, Sr-75, Kr-77, Ga-68, In-110, Br-76, Ga-66, Ga-72, Sb-122, Na-24, Si-31, Ge-77, Ho-166, Re-188, Bi-212, Y-90, K-42, Ir-192, I-125, Pd-103, Sr-90, and radioactive sodiumchloride, or any other chemical compound formulated from the isotopes given in Table 3, for example.

The radioactive coatings of the instant invention may be applied to the balloon portion of the catheter either at the time of manufacture or at the time of use, by the user. Additionally, bonding of the radioactive source to the ballon catheter material may also be performed either at the time of manufacture or at the time of use, by the user. A host of methods for attaching radioactive moieties to plastic surfaces are know. In general, proteins, nucleic acids, and smaller molecules may be adsorbed either covalently or by ionic bonding to various plastics (15–17). Also existing are techniques to radioactively modify proteins or nucleic acids (18–24). For additional plastic composition and radioactive source bonding data see (25) and the documents cited therein.

According to another aspect of the instant invention an apparatus guided by a guidewire within a patient's artery for receiving a radiation dose delivery wire with a radiation source encapsulated within its distal end and for reducing restenosis after arterial intervention in the patient's artery is provided, comprising a balloon catheter with a blind lumen sealed at its distal end and a guidewire lumen extending therethrough to accept said guidewire, said blind lumen being adapted to accept said radiation delivery wire into its proximal end.

The apparatus may further comprise means for moving the distal end of said radiation dose delivery wire to a predetermined position within said blind lumen for a predetermined period of time.

The apparatus may further comprise means for providing a liquid-tight seal between the radiation dose delivery wire and the proximal end of the blind lumen.

The means for providing a liquid-tight seal may comprise a liquid-tight radiation delivery wire port connected to the proximal end of the blind lumen, whereby a liquid-tight seal is effectuated between the proximal end of the blind lumen and the radiation dose delivery wire.

The means for moving may be a computer controlled afterloader.

The computer controlled afterloader may calculate said predetermined position and said predetermined time.

The computer controlled afterloader may calculate said predetermined position and said predetermined time based upon a plurality of input variables including a half-life of the radiation source, an activity level of the radiation source, a diameter of said artery, and a desired radiation dosage to be delivered to the artery at the predetermined position.

A user may input a plurality of values each representing respective ones of the plurality of input variables to the computer controlled afterloader.

The computer controlled afterloader may move said distal end of said radiation dose delivery wire back and forth in the area of the predetermined position for a predetermined period of time.

The following are dosimetric calculations for various isotopes and source geometries in an attempt to identify the most suitable source designs for such treatments.

Methods and Materials:

Analytical calculations are presented for dose distributions and dose rates for Ir-192, I-125, Pd-103, P32, and Sr-90 as they might pertain to intracoronary radiations. The effects of source size and positioning accuracy are studied.

Results:

Accurate source placement, dose rates >5Gray/minute, sharply defined treatment volume, and radiation safety are all of concern. Doses of 10–20 Gray are required to a length of 2–3 cm of vessel wall, which is 2–6 mm in diameter. The dose distribution must be confined to the region of the angioplasty, with reduced doses to normal vessels and myocardium. Beta particle or positron particle emitters have radiation safety advantages, but may not have suitable ranges for treating large diameter vessels. Gamma emitters deliver relatively large doses to surrounding normal tissues, and to staff. Low energy x-ray emitters such as I-125 and Pd-103 may represent a good compromise as might injecting a radioactive liquid directly into the angioplasty balloon.

Conclusions:

Accurate source centering is found to be the single most important factor for intracoronary irradiations. If this can be accomplished then a high energy beta particle or positron particle emitter such as Sr-90 would be the ideal source. Otherwise the gamma emitter Ir-192 may prove optimum. A liquid beta particle or positron particle source such as P-32 has the optimum geometry, but may be unsafe for use with currently available balloon catheters when formulated as a bone-seeking phosphate.

Several groups have presented data demonstrating that 10–20 Gray of acute radiation delivered locally, via the temporary insertion of high activity gamma emitters at the time of angioplasty can inhibit restenosis in animal models (12,13). It has also been demonstrated that permanent radioactive coronary stents may be effective (10). Highly localized external beam therapy has been suggested as well (7,11). Most data to date have been obtained using animal models, but anecdotal reports suggest that radioactive treatment of human femoral arteries produces similar results (2). Preliminary human trials are being planned at several centers in the U.S. and Europe.

Preliminary studies have made use of currently available radioactive sources as none have been specifically designed for intracoronary treatments. Several manufacturers are considering modified High Dose Rate (HDR) afterloaders for this purpose. It therefore seems appropriate to identify the most suitable isotope and source design for such a device.

The design criteria are formidable. Doses of 10–20 Gray are required to a length of 2–3 cm of the vessel wall, which is 2–6 mm in diameter. The dose distribution should be tightly confined to the region of the angioplasty, with greatly reduced doses to normal vessels and the myocardia. Dose rates on the order of 5 Gray/minute are required in order to maintain treatment times within tolerable limits. This immediately suggests HDR afterloading, perhaps with specially designed sources suitable for insertion into standard or modified catheters.

Current angiographic techniques utilize open ended catheters which are flexible enough to be pushed through >100 cm of artery, and able to negotiate multiple bends between the femoral and coronary arteries. They must also pass through vessels as small as 3 mm diameter with small radii of curvature. The radioactive source must have similar flexibility. Source integrity is of great importance as dislodgement into a coronary artery could be fatal.

Most intraluminal studies to date have used Ir-192 seeds of 10–20 mCi activity. Typical seed dimensions are 0.5 mm diameter, 3 mm length (Best Industries, Springfield VA). Multiple seed arrays are used with spacing 0.5 cm embedded in a 1 mm diameter plastic catheter. While these sources have proven useful for preliminary studies, the relatively high energy and low dose rates are not ideal. The need for specialized source and catheter design is obvious. For this reason, P-32, Sr-90, and other beta particle or positron particle emitters have been suggested.

Beta particle or positron particle emitters have obvious radiation safety advantages, useful for permitting treatments in the angiographic fluoroscopy suite. As we will show however beta particle or positron particle ranges may not be suitable for treating larger diameter vessels. Lower energy gamma and x-ray emitters such as I-125 and Pd-103 may represent a good compromise, but are not currently available at the required specific activities. Other possibilities include injecting a radioactive liquid directly into the angioplasty balloon.

We compare five isotopes for potential use in intracoronary irradiation: Ir-192, I-125, Pd-103, P-32, and Sr-90. While other suitable isotopes may exist, these five are all commercially available, although not necessarily in the form or activity required for intracoronary irradiation.

They also represent the three main categories of possible isotopes, namely high energy gamma emitter, low energy gamma/x-ray emitter, and beta particle or positron particle emitter. The basic properties of each isotope are given in Table 1.

Ir-192 undergoes beta minus decay, but the therapeutically useful radiations are the 7 de-excitation gammas of the daughter nucleus Pt-192 which range in energy from 296–612 keV with an average energy of 375 keV. I-125 and Pd-103 both decay via electron capture with the therapeutically useful radiations being primarily characteristic x-rays from the daughter nuclei, Te-125 and Rh-109, respectively.

P-32 is a pure beta minus emitter which decays directly to the ground state of S-32 with a transition energy of 1.71 MeV. Sr-90 is a pure beta minus emitter with a half life of 28 years. It decays to Y-90, also a pure beta particle or positron particle emitter with a half life of 64 hours. The strontium and yttrium are in radioactive equilibrium, with the higher energy yttrium beta particle or positron particles (2.27 versus 0.54 MeV transition energy) providing most of the therapeutically useful radiation.

Given these basic isotopic properties, we consider a source consisting of a small metallic seed, similar to those currently used for conventional brachytherapy and HDR. Seeds would have dimensions on the order of $\leq 1$ mm diameter and 1–3 mm length. Treatment with such a source would require either multiple sources on a line (such as those currently available for conventional afterloading), or programmable source placement (similar to conventional HDR units) to permit treatment of 2–3 cm of vessel wall. The source could in theory be inserted directly into the coronary artery, or more likely, inserted into a conventional or slightly modified balloon catheter. In either case, as we will show later, it is highly desirable that the source be centered within the coronary artery to insure a uniform dose to the arterial walls.

To optimize source design we need to know the radial dose distribution, and the dose rate per mCi activity. The axial dose distribution is of less concern, as this can be optimized by suitably weighting the source dwell times as in conventional HDR. We assume that for each of the isotopes listed in Table 1, a suitable source can be fabricated. For comparison purposes only we consider first a single source of 0.65 mm diameter and 5 mm length, with the axial position programmable to enable treatment of any length of arterial wall.

For gamma and x-ray emitters the radial dose distributions from point or line sources are well known on theoretical considerations. Many measurements have been reported as well, although measurements at distances less than several millimeters are difficult due to technical considerations. AAPM Task Group-43 (TG-43) (9) has reviewed the available data and presented recommendations for calculating dose:

$$\text{Dose }(r,\Theta)=S*\Gamma*G(r,\Theta)*g(r)*F(r,\Theta) \quad \text{Eq. 1}$$

where:

$S$=air kerma strength $\Gamma$=dose rate constant $r$=radial distance from source $\Theta$=angle from point of interest to center of source, as measured from the axial dimension of the source (we consider here $\Theta$=90°

$G$='geometry factor' resulting from spatial distribution of the radioactivity within the source. For a 3 mm long line source, $G(r,\Theta)=r^{-2}$ for $\Theta=90°$ $g$=radial dose function, given as $\Sigma_i a_i * r^i$, where:

$a_i$=fitted parameters to a fifth order polynomial $F$=anisotropy factor describing dose variation versus angle. This function is normalized to unity at $\Theta$=90°

In practice, for distances >1 cm and $\Theta$=90° all of the correction factors in Equation 1 are approximately unity as photon attenuation and photon scatter very nearly cancel. Williamson and Zi (14) have shown that for the Ir-192 sources currently used in HDR units radial errors (for $r \leq 1$ cm) are >1%, and anisotropy errors (for $30° \leq \Theta \leq 150°$) are >10%. Dose versus distance thus approximates the $1/r^2$ law except for the lowest energy x-ray sources. Specific details on all factors in Equation 1, as well as values for S, $\Gamma$, $a_i$, G, g, and F are found in TG-43 (9).

For beta minus emitters dose versus radial distance from a point source can be calculated more directly using the equation:

$$\text{Dose }(r)=\int_{E=0}^{E_{max}} F(E)*A*k*S(E')*p*dE/4\pi r^2 \quad \text{Eq. 2}$$

where:

$r$=distance in cm

F(E)=initial fluence of electrons with energy E

A=activity in mCi k=conversion factor from MeV-mCi/gm to Gy/min

S(E')=mean restricted stopping power for electron of energy E'in MeV/cm

E'=energy of electron with initial energy E at distance r from the source p=density Electron ranges and stopping powers were taken from Berger and Seltzer (1). F(E) spectra for P-32 and Sr-90 (in equilibrium with Y-90) were obtained from the literature (3,5).

The radial dose distributions given by Equations 1 and 2 were integrated over the axial length (L) of the source to properly correct for the distance 'r', and for Equation 1 the anisotropy factors. Thus at a radial distance 'r' from a source of axial length 'L':

$$\text{Dose}(r) = \int_{X=-L/2}^{+L/2} \text{Dose}(\text{Sqr. Root}(r^2 + x^2))dx \quad \text{Eq. 3}$$

where:

Dose (r) is given either by Equation 1 or 2.

For beta particle or positron particle sources it was assumed that the radioactive isotope was plated on the exterior surface of the seed, and that electron range was insufficient to pass through the seed. Thus, for each radial position, Equation 2 was integrated only over the solid angle of the source which is 'visible' at a distance 'r'. For x and gamma sources internal absorption is implicitly included in the factor $F(r,\Theta)$. Absolute dose rates in water per mCi activity were also calculated directly from Equations 1–3.

Figure 11:
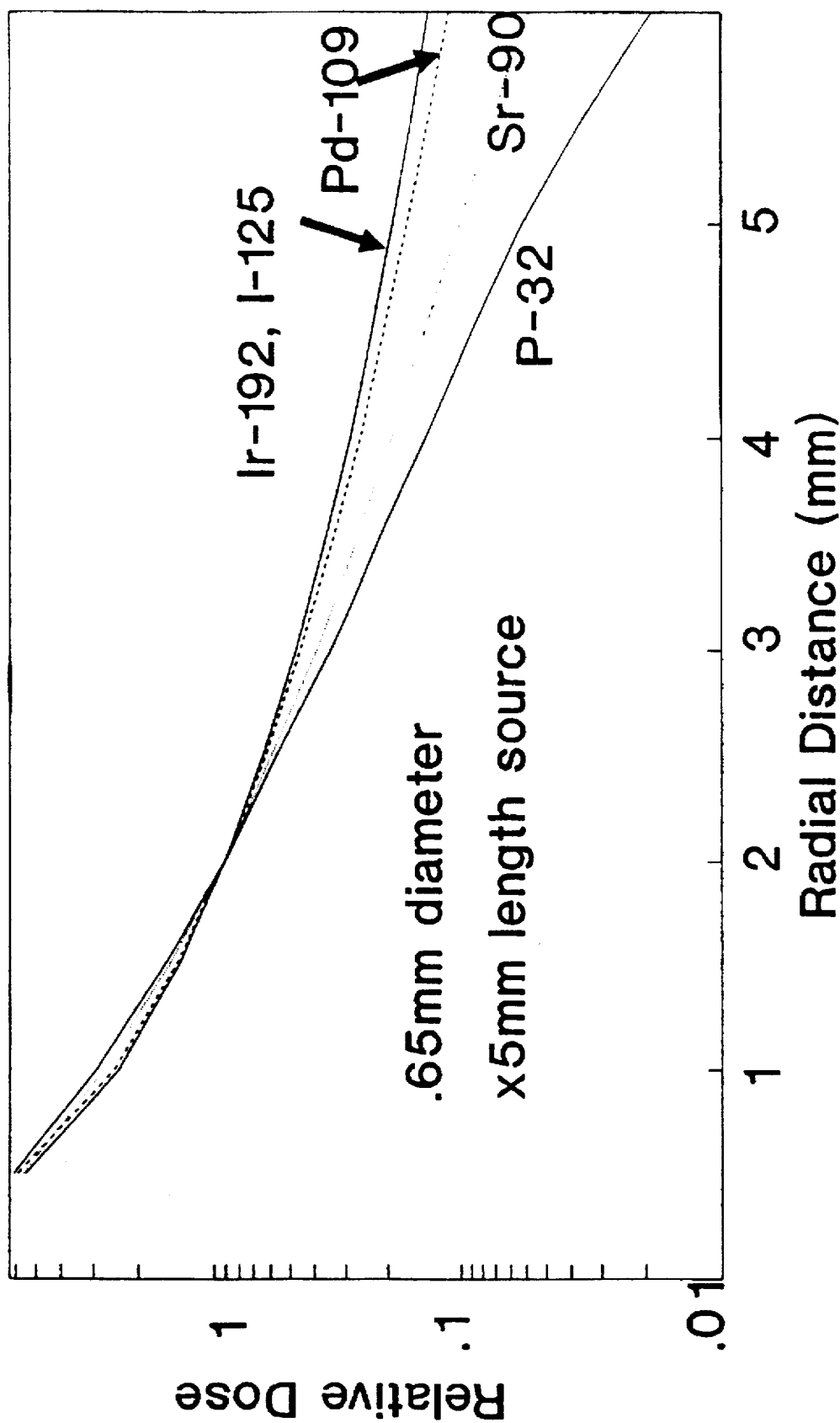
FIG. 11 shows dose versus distance for Ir-192, I-125, Pd-103, P-32, and Sr-90.

FIG. 11 presents relative dose versus radial distance for a source of 0.65 mm diameter, and 5 mm length, for each isotope. Doses are normalized to 1.00 at a distance of 2 mm, the approximate radius of a typical coronary artery.

Ir-192 and I-125 have nearly identical dose distributions, with both being very nearly equal to inverse square falloff of dose. Pd-103, because of its lower photon energy has a more rapid dose fall off, as attenuation becomes significant even at small distances.

The beta particle or positron particle emitters P-32 and Sr-90 show even more rapid dose fall off versus distance because of the large number of low energy electrons in their respective spectra which have concomitant short ranges. P-32, with a maximum energy of 1.7 MeV and mean energy of 0.690 MeV (versus 2.27 and 0.970 MeV for Sr-90/Y90) has the greatest dose fall off.

Source activities required to achieve a dose rate of 5 Gray/minute at a radial distance of 2 mm to a 2 cm length of arterial wall are given in Table 1. This equates to a 4 minute treatment time to deliver 20 Gray, varying with the diameter and axial extension of the treatment volume. As seen in Table 1, suitable X and gamma sources require activities ≧1 Ci, whereas beta particle or positron particle sources require only tens of mCi. Due to uncertainties in factors, source anisotropy, and dose variation at distances >0.5 cm the values given in Table 1 for required activity should be considered approximate.

Iridium (Best Industries, Springfield, Va.), Phosphorus (Mallinckrodt, Inc., Technical Product Data. St. Louis, Mo.), and Strontium(New England Nuclear, Boston Mass.) sources of suitable size and activity can readily be fabricated, although not all are currently commercially available. Iodine and Palladium on the other hand present technical problems in fabrication at this time.

Although the effect is more dramatic for beta particle or positron particle sources, FIG. 11 shows that even gamma sources have extremely rapid dose fall off with radial distance. Dose uniformity is thus critically dependent on centering the source with the artery.

Figure 12:
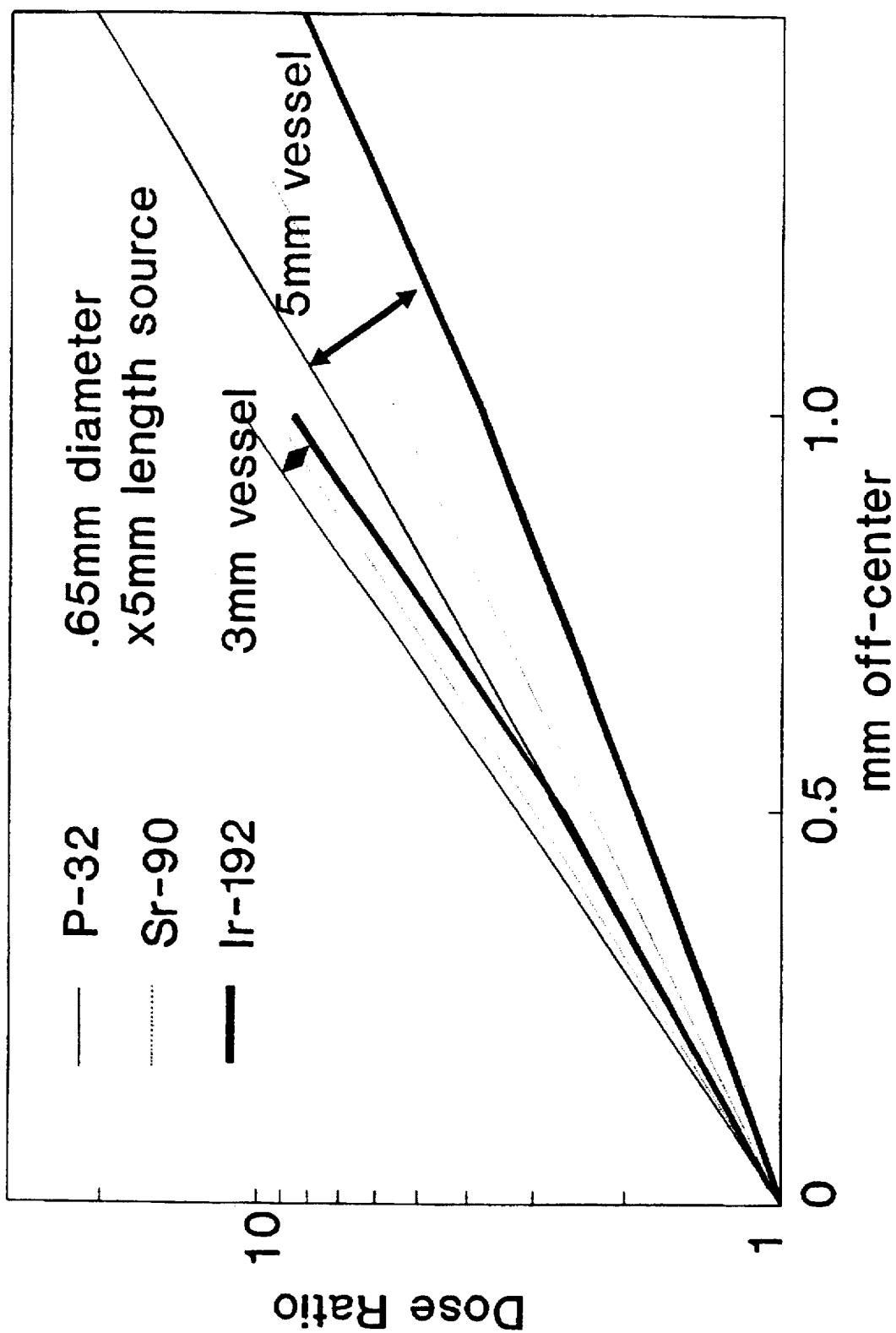
FIG. 12 shows dose asymmetry (defined as maximum/minimum dose to vessel wall) resulting from inaccurate centering of 5 mm long P-32, Sr-90, or Ir-192 sources within arteries of 3 and 5 mm diameter.

Dose asymmetry can be calculated from FIG. 11, and in FIG. 12 we demonstrate the magnitude of this asymmetry resulting from inaccurate centering of a single 5 mm long source of Sr-90, P-32, or Ir-192. Plotted are the ratios of maximum vessel dose to minimum vessel dose in vessels of 3 and 5 mm diameter as a function of centering error. As seen, centering errors as small as 0.5 mm in a 5 mm diameter vessel result in dose asymmetries ranging from 2.25 for Ir-192 to 2.62 for P-32. This corresponds to deviations from 'prescription dose' of +56% and −31% for Ir-192, and +60% and −30% for P-32. Expectedly, the magnitude of the dose asymmetry increases as source energy decreases. Ir-192 thus yields the smallest dose asymmetries, and P-32 the largest.

Figure 13:
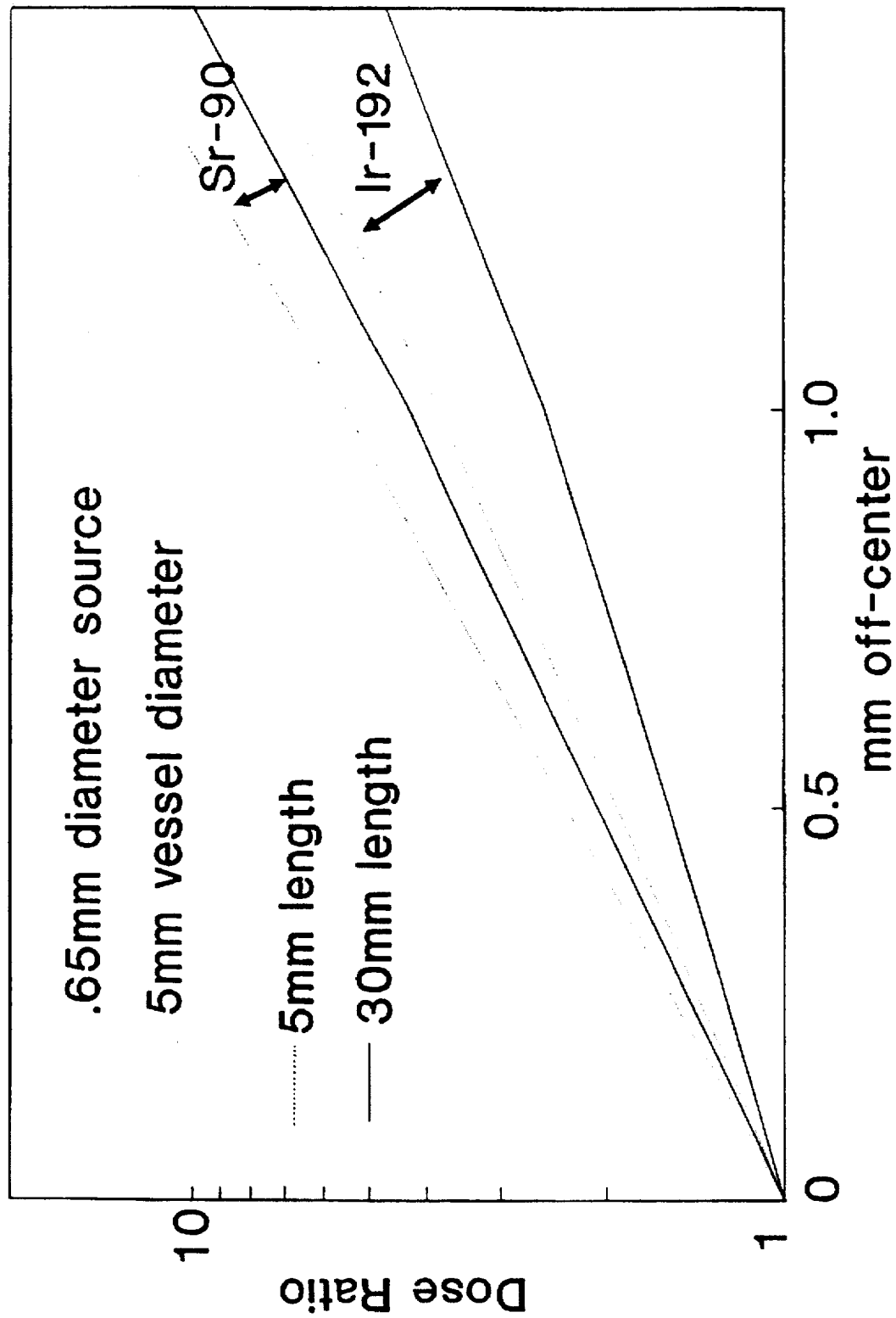
FIG. 13 shows a comparison of dose asymmetry for Sr-90 and Ir-192 sources of 5 and 30 mm length in a 3 mm diameter vessel.

If source position is programmed to treat a longer length of vessel wall dose asymmetries are slightly reduced because dose fall off versus radial distance is less rapid for a line source as compared to a point source. Accurate source positioning is still of major importance however, as FIG. 13 shows significant asymmetries even for a 3 cm long treatment volume in a 5 mm diameter vessel.

Figure 14:
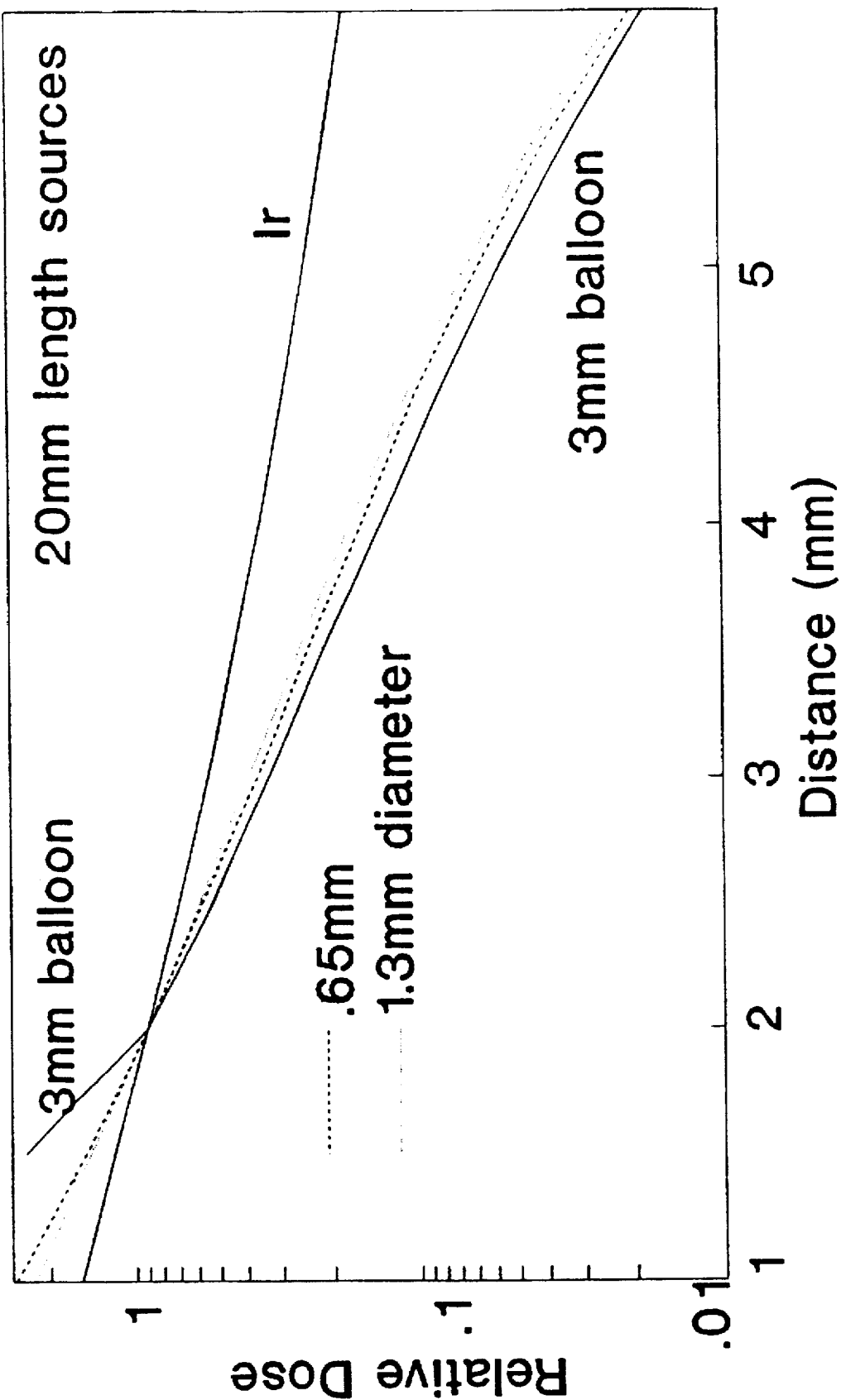
FIG. 14 shows radial dose distribution for P-32 wires of 0.65 and 1.3 mm diameter, and for a 3 mm diameter P-32 balloon.

For any source the radial dose distribution (and subsequent error resulting from inaccurate source positioning) can be slightly improved by increasing the source thickness, but this has obvious limitations in terms of source flexibility. FIG. 14 shows that for treatment of a 2 cm length of vessel increasing the diameter of a P-32 source from 0.65 to 1.3 mm results in a marginal improvement in dose distribution. Thus, for all sources a minimum size is optimum.

The dosimetric asymmetry introduced by errors in source positioning can be eliminated if we consider the possibility of using a liquid beta particle or positron particle emitter such as P-32 sodium phosphate solution, which could be injected directly into the angioplasty balloon, or even coated onto its inner surface. Balloons are normally inflated with contrast, but they could, in principle, be inflated with P-32 solution. This would have the distinct advantage of guaranteeing that the radioactive source is in the correct position, and in direct contact with the vessel walls, thus optimizing dose uniformity.

A typical balloon is 2–3 cm in length (1), and is inflated to the full diameter (d) of the vessel. Depending on the degree of arterial occlusion, a 2 cm long balloon inflated to a diameter of 3 mm would have a total volume of approximately 0.14 ml (i.e., volume=$\Pi d^2$¼). The resulting radial dose distribution of the balloon can be calculated using a slightly modified formulation of Equations 2 and 3, where the integration is extended over the radial extent of the source. The equations describing this have been given in reference (10). The resulting dose distribution is similar to that of P-32 coated seed or wire, as shown in FIG. 14, which compares doses for 20 mm length wires and a balloon.

A dose rate of 5 Gray per minute could be achieved from a balloon filled with a solution of approximately 50 mCi/ml specific activity. The catheter running from the femoral to the coronary artery would also be filled with radioactive solution, but since the diameter of this tube is ≦0.4 mm (Medtronic Inc., Deerfield Beach, Fla. ), the dose rate to normal vessels around this tube would be less than 20% of the treatment dose, depending on the diameter of the vessels. A 20 Gray treatment would result in less than 4 Gray to normal vessel—well below normal tissue tolerance.

We are thus left with a choice between high energy gamma or beta particle or positron particle emitters. The desired criteria for a source are: high dose rate per mCi; high specific activity; long half life; and treatment distance of at least 3–4 mm.

No available isotope is ideal. Sr-90 has advantages in terms of specific activity, dose rate, radiation safety, and half life; while Ir-192 has an advantage in terms of radial dose distribution. Both isotopes could be fabricated at the required specific activities using current technology.

There is a trade off between the increased radial range of Ir-192, and the safety advantages of Sr-90. Although it is a qualitative assessment, it appears from FIG. 11 that if the radial treatment distance was always ≦1.5 mm, Sr-90 would be the isotope of choice. For larger treatment distances, Ir-192 would be better.

The argument however hinges on one's ability to center the radioactive source in the artery. If ideal centering were possible then any source would provide radial dose homogeneity and Sr-90 would be the isotope of choice. Current catheter design however dose not guarantee centering, and the increased range of Iridium could be of advantage.

Based upon dose distributions, dose rate, specific activity, and commercial feasibility both Ir-192 and Sr-90 could be suitable sources for intracoronary irradiation. Higher energy beta particle or positron particle sources would be highly desirable, but these invariably have extremely short half lives. We have shown here that P-32, with a transition energy of 1.7 MeV is marginally acceptable as a possible source, so one can rule out any isotopes with lower transition energies. Isotopes with shorter half lives (14 days for P-32) would also prove to be impractical.

On the other end of the beta particle or positron particle spectrum, there are no isotopes with half lives greater than Sr-90 (28 years) that also have a greater transition energy (2.27 MeV for Sr-90's daughter Y-90). This seems to make Sr-90 the beta isotope of choice, although other possibilities exist, such as Sb-124 with a half life of 60 days and average energy of 918 keV. Dose distributions for other beta particle or positron particle isotopes are similar to those shown in FIG. 11, and development of such sources would not alter our basic conclusions.

The introduction of P-32 solution directly into the angioplasty balloon is particularly attractive in that it eliminates all problems of dose inhomogeneity and range. With current technology catheters however there is a 1–2% occurrence of balloon failure. If the balloon and 100 cm length of catheter were completely filled with P-32 solution, and if the balloon failed, there could then be as much as 15 mCi of P-32 released directly into the blood. Since P-32 as the phosphate moiety is a bone seeking isotope (occasionally used for the treatment of polycythemia vera), this could result in a skeletal dose >9.5Gy, and a whole body dose >1.5Gy$^2$ (8)—both unacceptable risks. Alternatively, other chemical forms of P-32, more rapidly cleared, would not home to the bone marrow and therefore have an acceptable toxicity profile. Still, the dosimetric advantages of such a treatment seem to warrant further studies of catheter design. Another possible solution to this problem would be to identify a beta particle or positron particle emitter whose chemical formulation would be more benign and have shorter biological half lives. Such radioactive solutions may be selected from the group consisting of fluids containing Cu61, Se-73, Co-55, Sc-44, Sr-75, Kr-77, Ga-68, In-110, Br-76, Ga-66, Ga-72, Sb-122, Na-24, Si-31, Ge-77, Ho-166, Re-188, Bi-212, Y-90, K-42, Ir-192, I-125, Pd-103, Sr-90, and radioactive sodium-chloride, or any other chemical compound formulated from the isotopes given in Table 3, for example. At current prices, Ir-192, Sr-90, and P-32 sources of the required activities could all be fabricated for approximately $10³–10⁴, not counting development costs. Sr-90 has by far the longest half life (28 years), with Ir-192 (74 days) and I-125 (60 days) lagging far behind. Cost may therefore be a significant factor in source selection.

FIG. Captions

11. Radial dose versus distance for Ir-192, I-125, Pd-103, P-32, and Sr-90. Sources are 0.65 mm diameter and 5.0 mm length. Doses have been normalized to 1.0 at a radial treatment distance of 2.0 mm.
12. Dose asymmetry (defined as maximum/minimum dose to vessel wall) resulting from inaccurate centering of 5 mm long P-32, Sr-90, or Ir-192 sources within arteries of 3 and 5 mm diameter. When the source is centered in the artery, the dose asymmetry is 1.0.
13. Comparison of dose asymmetry for Sr-90 and Ir-192 sources of 5 and 30 mm length in a 5 mm diameter vessel. When the source is centered in the artery, the dose asymmetry is 1.0.
14. Radial dose distribution for P-32 wires of 0.65 and 1.3 mm diameter, and for a 3 mm diameter P-32 balloon. All sources are 20 mm length. The dose for a 20 mm length Ir-192 source is shown for comparison. Doses have been normalized to 1.0 at a radial treatment distance of 2.0 mm.

Figure 2:
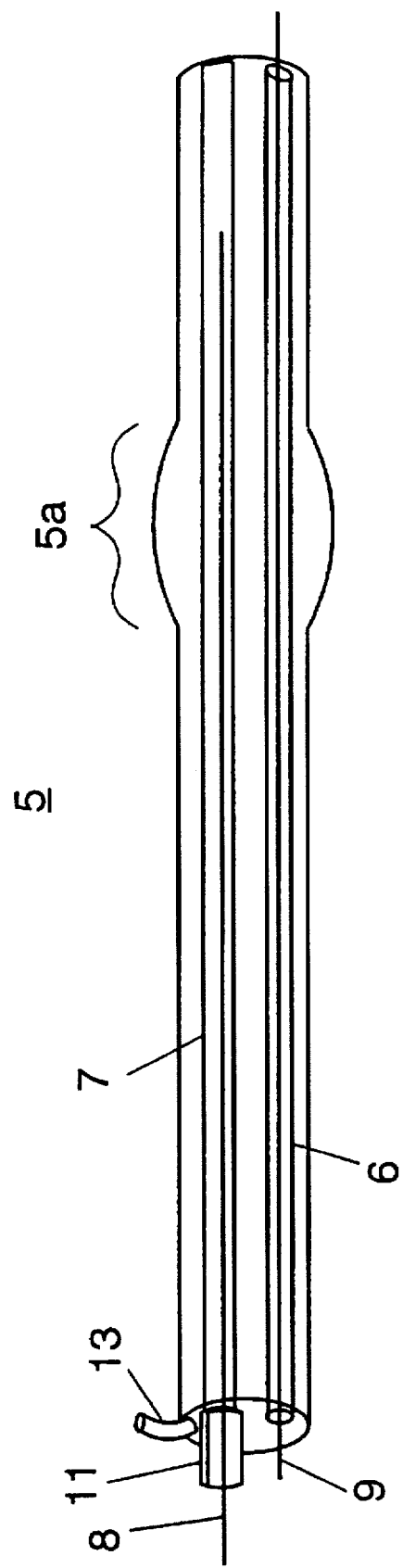
FIG. 2. shows the construction of a balloon catheter according to a first embodiment of the present invention.

Referring now to the FIGS., FIG. 2 shows a balloon catheter according to a first embodiment of the present invention, which can be used to perform the method according to the present invention. The apparatus is particularly suited for delivering radioactive doses to the coronary artery. The preferred embodiment will be described with reference to the coronary artery, but this is by way of example, and not limitation, as the present invention may also be used to deliver radiation to peripheral arteries.

The apparatus comprises a balloon catheter 5 with a guidewire lumen 6 extending entirely through the balloon catheter 5 and a blind lumen 7 which is closed at the distal end of the balloon catheter 5, for receiving a radiation dose delivery wire 8. The guidewire lumen 6 is sized to fit around a guidewire 9 and to allow the guidewire 9 to slide therein. The length of guidewire 9 is sufficient to allow it to extend past a target segment of the artery and it may be, for example, greater than about 110 cm for use in the coronary artery. For use in other arteries, the length of guidewire 9 may also be greater than about 110 cm or it may be less.

The outside diameters of the guidewire 9 and the radiation dose delivery wire 8 may be about 0.014 inch and in this case the inside diameters of the guidewire lumen 6 and the blind lumen 7 are slightly larger, to permit movement of the balloon catheter 5 over the guidewire 9 and movement of the radiation dose delivery wire 8 through blind lumen 7.

The radiation dose delivery wire entry port 11, at the proximal end of the balloon catheter 5, is adapted to receive the radiation dose delivery wire 8 and to provide a watertight seal. Thus, the radiation dose delivery wire 8 is isolated from contact with the patient's body fluids. The balloon inflation port 13 allows inflation of the balloon section 5a at the distal end of the balloon catheter 5 in the conventional manner.

Figure 3:
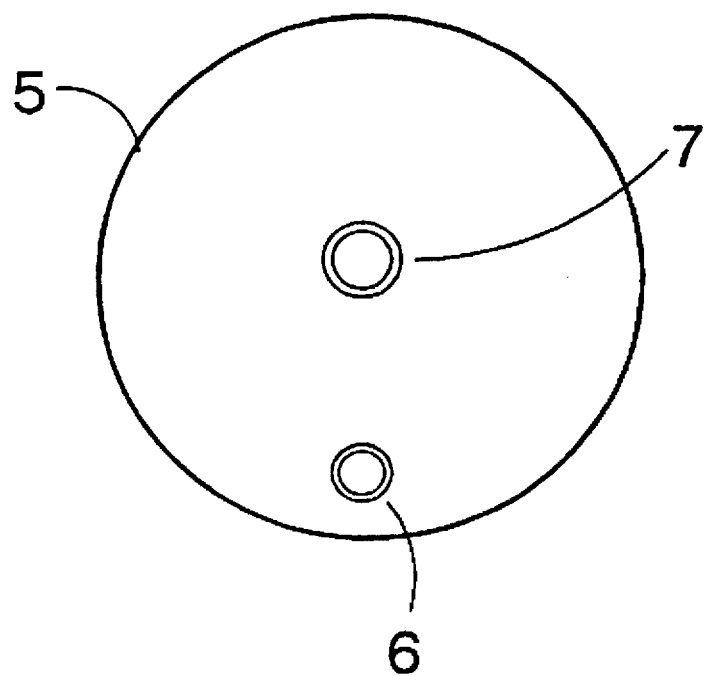
FIG. 3 shows a cross-section of the balloon catheter according to the first embodiment of the present invention.

Referring now to FIG. 3, wherein the same reference numerals of FIG. 2 are applied to the same parts and therefore do not require detailed description, it is seen that the guidewire lumen 6 may be off center with regard to the balloon catheter 5, while the blind lumen 7, which is adapted to encircle the radiation dose delivery wire 8, may be substantially in the center of the balloon catheter 5.

Figure 4:
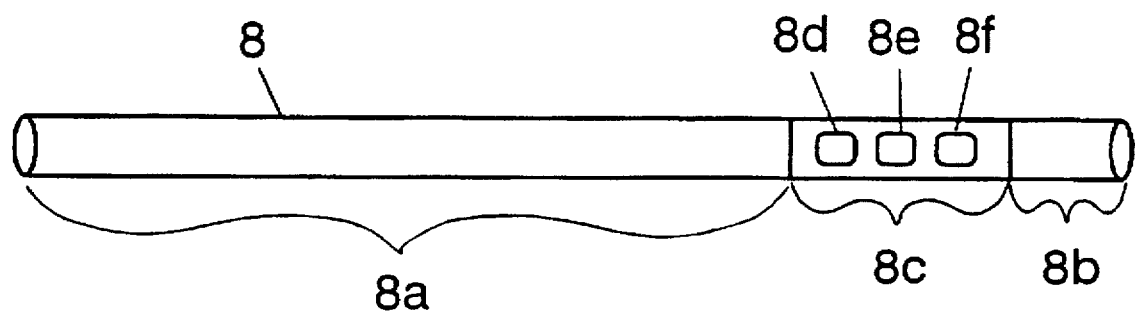
FIG. 4 shows the construction of a radiation dose delivery wire of the present invention.

Referring now to FIG. 4, wherein the same reference numerals of FIG. 2 are applied to the same parts and therefore do not require detailed description, it is seen that the radiation dose delivery wire 8 may include non-radioactive sections 8a and 8b and radioactive section 8c, which has encapsulated within the distal end of radiation dose delivery wire 8, a linear array of radioactive sources 8d, 8e, and 8f, such as pellets of $Ir^{192}$, $I^{125}$, $Pd^{103}$, or other isotopes selected from Table 4, for example. The length of the linear array of pellets may be less than or equal to about 2 cm for use in the coronary artery and less than or equal to about 10 cm for use in periphery arteries. Alternatively, the radioactive source may be composed of a non-linear array of such radioactive pellets or it may be composed of a single radioactive pellet. The radioactivity of each of the radioactive sources 8d, 8e, and 8f may be less than or equal to 10 Curies.

The operation of an apparatus to reduce restenosis after arterial intervention according to the first embodiment of the present invention is as follows. The guidewire 9 is inserted into the patient's artery. The distal end of the guidewire 9 is inserted at least as far as, and preferably past the target site, that is, the site that is to receive the dose of radiation. The guidewire 9 is then inserted into the guidewire lumen 6 and the balloon catheter 5 is moved down the guidewire towards the distal end until the balloon section 5a is adjacent the target site. In the case of a balloon angioplasty procedure the balloon section 5a is then inflated and deflated by balloon inflation/deflation inflation means (not shown) connected to the balloon inflation port 13. Alternatively, if it is desired to deliver a dose of radiation to the target area without inflating and deflating the balloon section 5a, such as following an atherectomy or other arterial intervention, the balloon section 1a need not be inflated and deflated.

Finally, the radiation dose delivery wire 8 is inserted into the proximal end of the blind lumen 7 within the balloon catheter 5 through the radiation dose delivery wire entry port 11. The radiation dose delivery wire 8 is inserted towards the distal end of the balloon catheter 5 until the radioactive sources 8d, 8e, and 8f are substantially adjacent the target area. The radioactive sources 8d, 8e, and 8f are left in place until a desired dosage of radiation has been delivered to the target area and then the radiation dose delivery wire 8 is removed from the balloon catheter 5. The length of time that the radioactive sources 8d, 8e, and 8f are left adjacent the target area depends upon the activity of the radioactive sources 8d, 8e, and 8e, the diameter of the artery at the target area, and the desired dosage to be delivered. It should be noted that the radiation dose delivery wire 8 may be oscillated back and forth within the blind lumen 7 so that the radioactive sources 8d, 8e, and 8f may be shorter than the target area while still being able to deliver radiation to the entire target area. In addition, if the radiation dose delivery wire 8 is oscillated back and forth, the time that the radioactive sources 8d, 8e, and 8f must be left adjacent the target area in order to deliver a desired dosage of radiation will also depend upon the length of the target area.

Alternatively, the guidewire 9 may be inserted into the artery as above and a conventional balloon catheter without a blind lumen placed over the guidewire 9 and advanced to the target area to be inflated, deflated, and removed from the artery. After removal from the artery, the balloon catheter 5 of the instant invention, with the blind lumen 7 may be placed over the guidewire 9 utilizing the guidewire lumen 6 and inserted adjacent the target area in order to allow the radiation dose delivery wire 8 to be inserted into the blind lumen 7 to deliver a dosage of radiation to the target area as described above. This procedure permits the use of a conventional balloon catheter to perform an angioplasty procedure before the balloon catheter 5 of the instant invention is utilized to deliver a dose of radiation.

Figure 5:
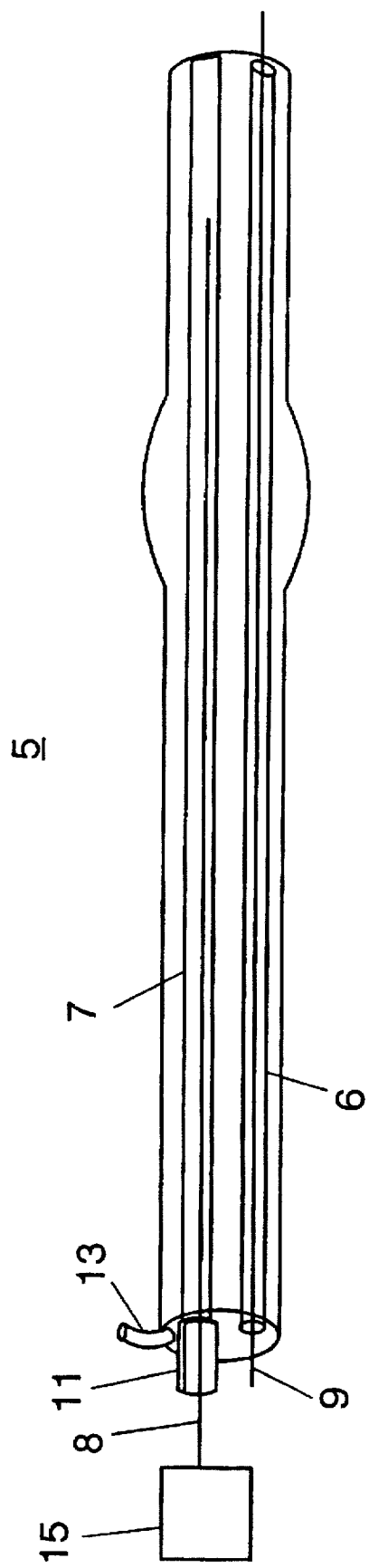
FIG. 5 shows the construction of a second embodiment of the present invention.

Referring now to FIG. 5, wherein the same reference numerals of FIG. 2 are applied to the same parts and therefore do not require detailed description, a balloon catheter according to a second embodiment of the present invention is shown, which can be used to perform the method according to the present invention. In this FIG., a computer controlled afterloader 15, similar to a conventional afterloader such as the one distributed by Nucletron Corp., of Columbia, Md., is connected to the proximal end of the radiation dose delivery wire 8 and is utilized to insert the radiation dose delivery wire 8 into the blind lumen 7 until the radioactive sources 8d, 8e, and 8f are adjacent the target area and to remove the radiation dose delivery wire 8 from the blind lumen 7 after a predetermined dosage of radiation has been delivered to the target area.

The computer controlled afterloader 15 of the present invention differs from the conventional afterloader in that the computer controlled afterloader 15 of the present invention allows an operator to input variables representing the activity of the radioactive sources 8d, 8e, and 8f, the date that the radioactive sources 8d, 8e, and 8f are being delivered adjacent the target area (to take into account decay of the radioactive sources 8d, 8e, and 8f), the diameter of the artery at the target area, the length of the target area, and the value of the desired radioactive dose to be delivered to the target area. The computer controlled afterloader 15 then calculates the time that the radioactive sources 8d, 8e, and 8f must be adjacent the target area to deliver the desired radioactive dosage and then moves the radiation dose delivery wire 8 towards the distal end of the balloon catheter 5 until the radioactive sources 8d, 8e, and 8f are adjacent the target area, waits the calculated time, and then pulls the radiation dose wire 8 back out of the balloon catheter 5.

In addition, the computer controlled afterloader 15 may oscillate the radiation dose delivery wire 8 back and forth while the radioactive sources 8d, 8e, and 8f are adjacent the target area. In this case the computer controlled afterloader 15 would take into account the length of the target area and the rate of oscillation in determining the time necessary to deliver the desired dosage.

The computer controlled afterloader 15 may include a program memory for storing a program to calculate the length of time that the radioactive sources 8d, 8e, and 8f must be adjacent the target area to deliver a desired dosage of radiation, a power supply backup, and a database memory for storing the number of times that a particular radioactive source has been used.

Figure 6:
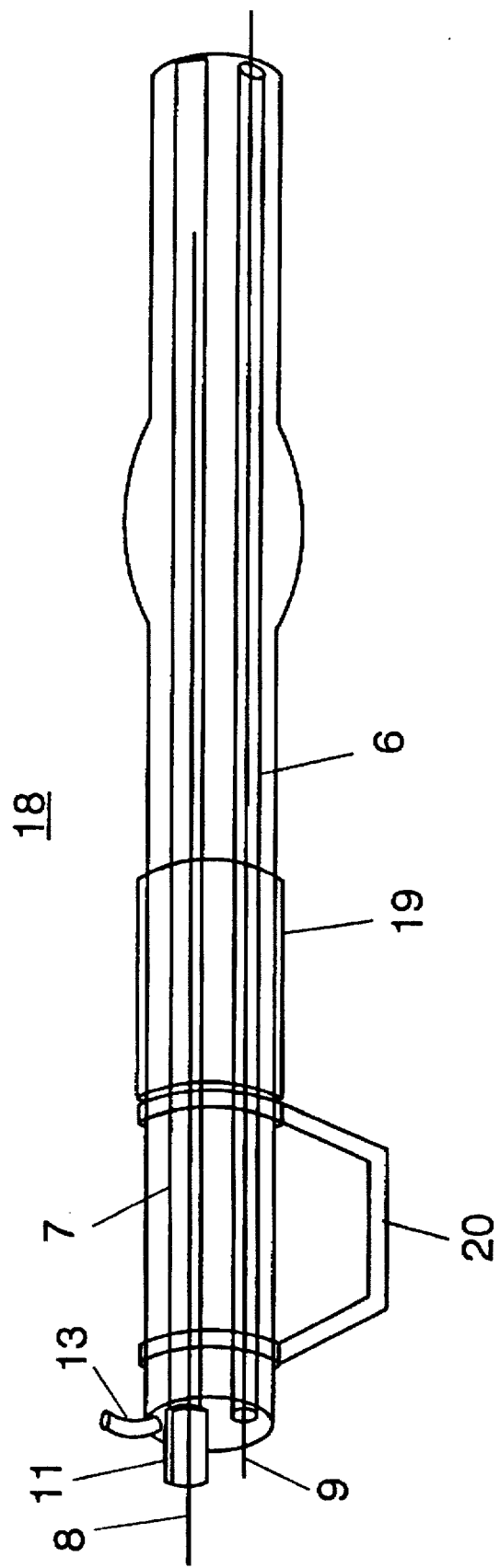
FIG. 6 show the construction of a third embodiment of the present invention.

Referring now to FIG. 6, wherein the same reference numerals of FIG. 2 are applied to the same parts and therefore do not require detailed description, a balloon catheter 18 according to a third embodiment of the present invention is shown, which can be used to perform the method according to the present invention. A clamp 20 may be utilized to maintain an extended coaxial position between the radiation dose delivery wire entry port 11 connected to the proximal end of the blind lumen 7 and a proximal end of a sheath 19, which surrounds catheter 18 at the area of the incision in the patient's body, during insertion of the radiation dose delivery wire 8 into the blind lumen 7.

Figure 7:
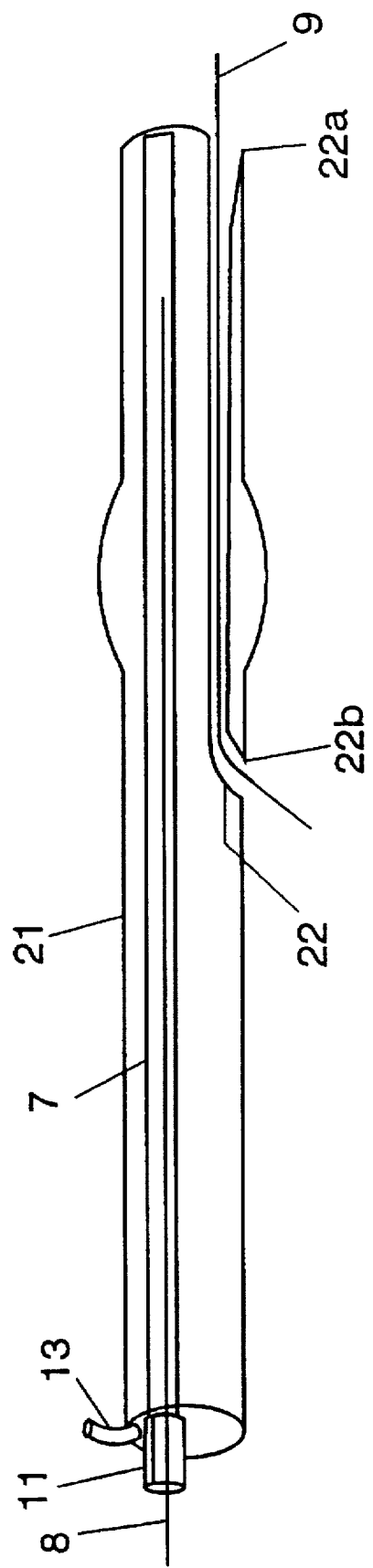
FIG. 7 shows the construction of a fourth embodiment of the present invention.

Referring now to FIG. 7, wherein the same reference numerals of FIG. 2 are applied to the same parts and therefore do not require detailed description, a balloon catheter 21 according to a fourth embodiment of the present invention is shown, which can be used to perform the method according to the present invention. In this Fig., a guidewire lumen 22 extends for a distance less than the length of the balloon catheter 21. That is, the guidewire lumen 22 has an entry point 22a at the distal end of balloon catheter 21 and exit point 22b along the length of balloon catheter 21, rather than at its proximal end.

As in the first embodiment, the guidewire 9 is inserted into the artery and the guidewire lumen 22 guides the balloon catheter 21 towards the distal end of the guidewire 9. Also, as in the first embodiment, the radiation dose delivery wire 8 rides within the blind lumen 23 of the balloon catheter 21.

Figure 8:
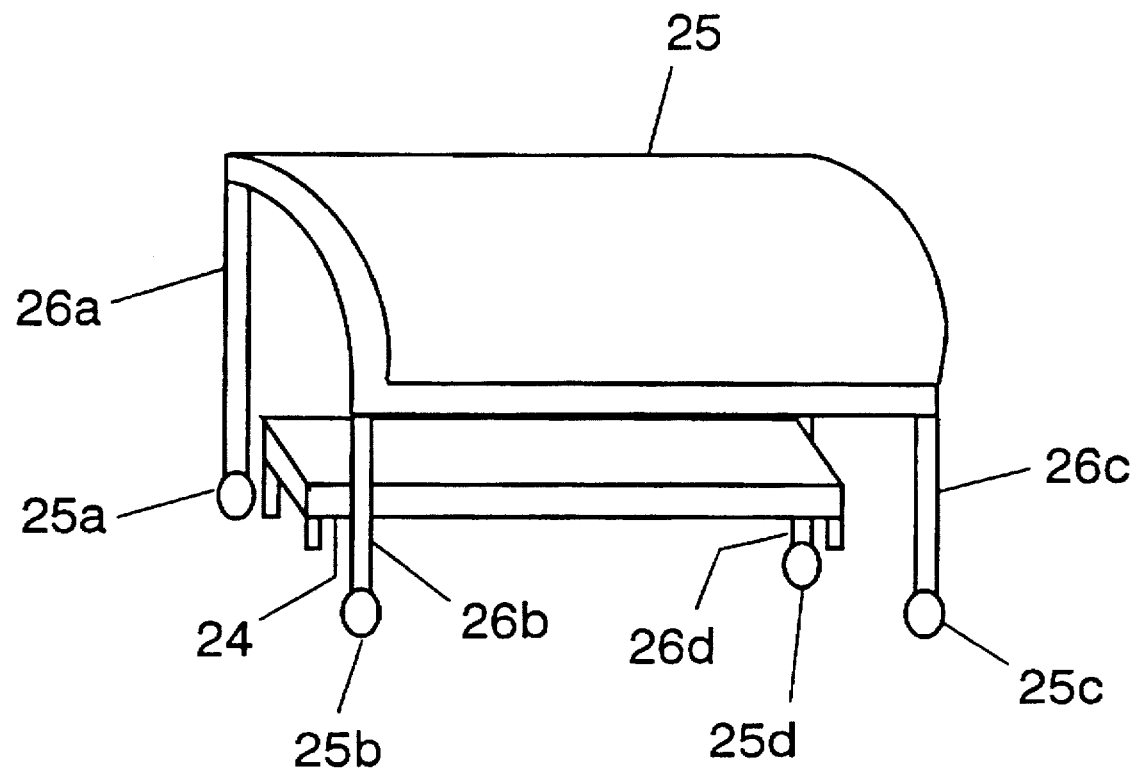
FIG. 8 shows the construction of a fifth embodiment of the present invention.

Referring now to FIG. 8, wherein the same reference numerals of FIG. 2 are applied to the same parts and therefore do not require detailed description, an apparatus according to a fifth embodiment of the present invention is shown, which can be used to perform the method according to the present invention. In this Fig., a radiation shield 25 is movable and is adapted to be moved between a patient (not shown) on a support 24 and an operator of the apparatus (not shown). The radiation shield 25 may, for example, be moveable by means of rollers 25a, 25b, 25c, and 25d mounted to legs 26a, 26b, 26c, and 26d.

In operation the balloon catheter 5, not shown in this FIG. 8, is inserted into a patient (not shown) who is supported by the support 24 and the radiation shield 25 is moved between an operator of the apparatus and the radiation source 8d, 8e, and 8f within the blind lumen 7 of the balloon catheter 5. The radiation shield 25 is thus adaptable for different sized patients because it is movable and it therefore provides protection to the doctor and other staff from over-exposure to radiation.

Figure 9:
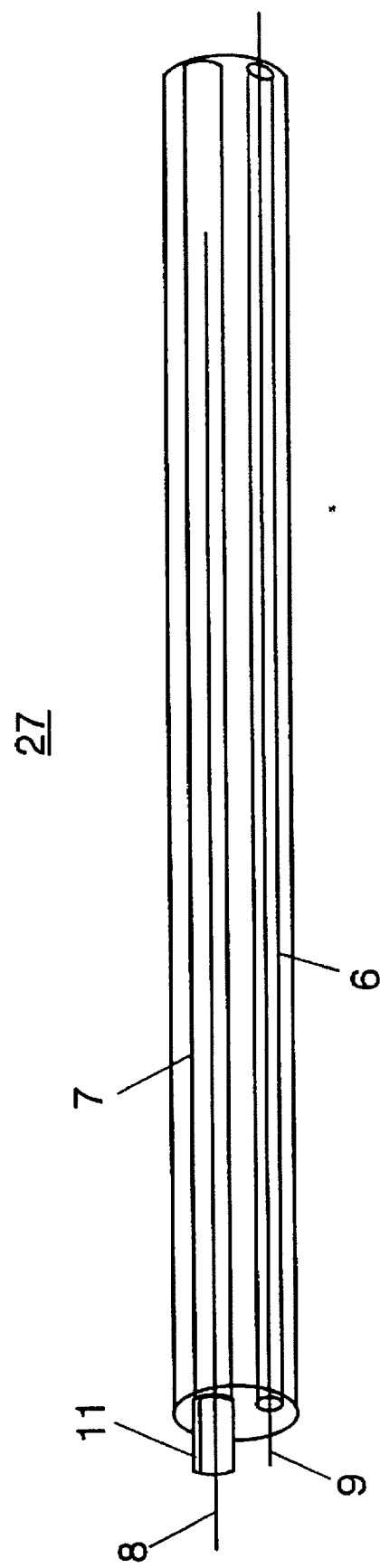
FIG. 9 shows the construction of a sixth embodiment of the present invention.

Referring now to FIG. 9, wherein the same reference numerals of FIG. 2 are applied to the same parts and therefore do not require detailed description, an apparatus according to a sixth embodiment of the present invention is shown, which can be used to perform the method according to the present invention. In this Fig., a catheter without a balloon 27 includes blind lumen 7 and guidewire lumen 6. This embodiment is utilized in a fashion similar to the first embodiment, except here, the apparatus is used only to deliver radiation, and does not have the balloon function of the first embodiment.

Figure 10:
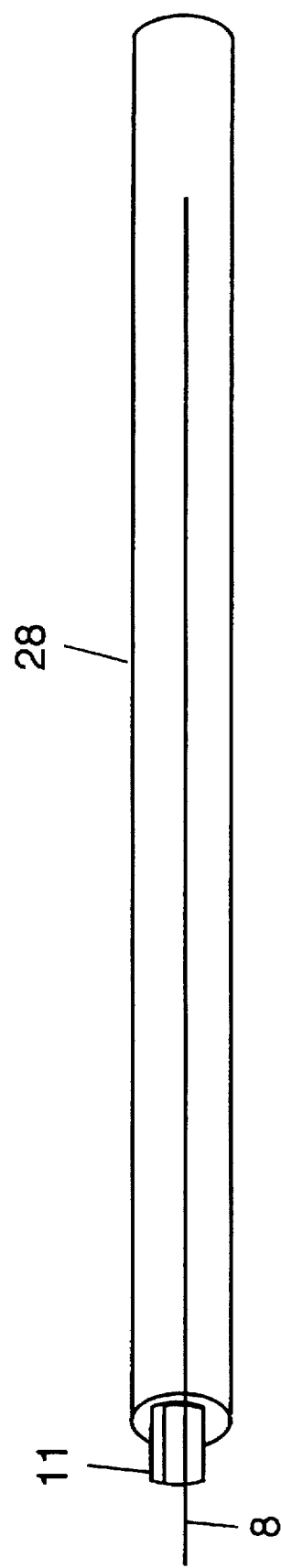
FIG. 10 shows the construction of a seventh embodiment of the present invention.

Referring now to FIG. 10, wherein the same reference numerals of FIG. 2 are applied to the same parts and therefore do not require detailed description, an apparatus according to a seventh embodiment of the present invention is shown, which can be used to perform the method according to the present invention. In this Fig., a blind lumen 28, which accepts radiation dose delivery wire 8 into its proximal end through radiation dose delivery wire entry port 11, is adapted to be removably inserted into a catheter (not shown). The catheter may be a balloon type catheter or it may be a catheter without a balloon.

In operation, the catheter is inserted into a patient in the conventional manner. Blind lumen 28 is then inserted into the catheter and, as in the first embodiment, the radiation dose delivery wire 8 is advanced into the blind lumen 28, through the radiation dose deliver wire entry port 11, until the distal end of the radiation dose delivery wire 8 is adjacent the segment of artery that is to receive a radioactive dose. Also, as in the first embodiment, the radiation dose delivery wire 8 is withdrawn after a desired dose of radiation has been delivered to the artery segment. This embodiment is intended primarily, but not exclusively, for procedures in the peripheral vascular areas.

It must be noted that although the present invention is described by reference to particular embodiments thereof, many changes and modifications of the invention may become apparent to those skilled in the art without departing from the spirit and scope of the invention as set forth in the claims.

TABLE 1

Basic Properties of Isotopes

| isotope | decay | emission | maximum energy | average energy | t½ | gamma factor[1] | activity[2] |
|---|---|---|---|---|---|---|---|
| Ir-192 | beta- | gamma | 612 keV | 375 kev | 74 d | 4.6 | 1000 mCi |
| I-125 | EC | x-ray | 35 keV | 28 kev | 60 d | 1.2 | 3700 mCi |
| Pd-103 | EC | x-ray | 21 keV | 21 keV | 17 d | 1.1 | 3700 mCi |
| P-32 | beta- | beta- | 1.71 MeV | 690 keV | 14 d | - | 36 mCi |
| Sr-90 | beta- | beta- | 2.27 MeV | 970 keV[3] | 28 yr | - | 30 mCi |

[1] R-cm2/hr-mCi
[2] For dose rate of 5 Gy/min at 2 mm distance, source diameter = 0.65 mm, length = 2.0 cm
[3] In equilibrium with Y-90

TABLE 2

| A | ELEMENT | Decay Mode | Half-Life | Rad. Type | | average Radiation Energy (keV) | | Radiation Intensity (%) | |
|---|---|---|---|---|---|---|---|---|---|
| 26 | AL 0.947 | EC | 7.4E + 5 Y 3 | B+ | | 543.49 | 7 | 81.77 | 17 |
| 123 | SN 1.11 | B- | 129.2 D 4 | B- | TOT | 522.7 | 14 | 100.00 | 13 |
| 123 | SN 1.11 | B- | 129.2 D 4 | B- | | 525.5 | 13 | 99.37 | 11 |
| 40 | K 1.07 | B- | 1.277E + 9 Y | B- | | 560.64 | 18 | 89.27 | 13 |

TABLE 2-continued

| A | ELEMENT | Decay Mode | Half-Life | Rad. Type | | average Radiation Energy (keV) | | Radiation Intensity (%) | |
|---|---|---|---|---|---|---|---|---|---|
| 89 | 3R 1.24 | B- | 50.53 D 7 | B- | | 583.3 | 13 | 99.99039 | 8 |
| 91 | Y 1.29 | B- | 58.51 D 6 | B- | TOT | 603.4 | 9 | 100.00 | 7 |
| 91 | Y 1.28 | B- | 58.51 D 6 | B- | | 604.9 | 9 | 99.70 | 5 |
| 115 | CD 1.29 | B- | 44.6 D 3 | B- | TOT | 605.2 | 10 | 99.98 | |
| 115 | CD 1.07 | B- | 44.6 D 3 | B- | | 618.3 | 9 | 97.00 | |
| 89 | SR 1.24 | B- | 50.53 D 7 | B- | | 583.3 | 13 | 99.99039 | 8 |
| 91 | Y 1.29 | B- | 58.51 D 6 | B- | TOT | 603.4 | 9 | 100.00 | 7 |
| 91 | Y 1.28 | B- | 58.51. D 6 | B- | | 604.9 | 9 | 99.70 | 5 |
| 115 | CD 1.29 | B- | 44.6 D 3 | B- | TOT | 605.2 | 10 | 99.98 | |
| 115 | CD 1.28 | B- | 44.6 D 3 | B- | | 618.3 | 9 | 97.00 | |
| 86 | RB 1.42 | B- | 18.631 D 1 | B- | TOT | 668.1 | 10 | 100.00 | 6 |
| 32 | P 1.48 | B- | 14.26 D 4 | B- | | 694.9 | 3 | 100.0 | |
| 86 | RB 1.38 | B- | 18.631 D 1 | B- | | 709.3 | 9 | 91.36 | 4 |

TABLE 3

| A | ELEMENT | Decay Mode | Half-Life | Rad. Type | | Radiation Energy (keV) | | Radiation Intensity (%) | |
|---|---|---|---|---|---|---|---|---|---|
| 43 | SC 0.767 | EC | 3.891 H 12 | B+ | | 508.1 | 9 | 70.9 | 6 |
| 61 | CU 0.569 | EC | 3.333 H 5 | B+ | | 524.2 | 5 | 51. | 5 |
| 73 | SE 0.778 | EC | 7.15 H 8 | B+ | | 562. | 5 | 65.0 | 7 |
| 73 | SE 0.789 | EC | 7.15 H 8 | B+ | TOT | 564. | 5 | 65.7 | 7 |
| 55 | CO 0.917 | EC | 17.53 H 3 | B+ | TOT | 567.07 | 21 | 76. | 4 |
| 44 | SC 1.27 | EC | 3.927 H 8 | B+ | | 632.6 | 9 | 94.34 | 4 |
| 90 | NB 0.721 | EC | 14.60 H 5 | B+ | | 662.2 | 18 | 51.1 | 18 |
| 75 | BR 1.09 | EC | 96.7 M 13 | B+ | TOT | 710. | 10 | 72 | 6 |
| 75 | BR 0.721 | EC | 96.7 M 13 | B+ | | 749. | 10 | 52. | 4 |
| 75 | BR 1.09 | EC | 96.7 M 13 | B+ | TOT | 710. | 10 | 72. | 6 |
| 75 | BR 0.830 | EC | 96.7 M 13 | B+ | | 749. | 10 | 52. | 4 |
| 85 | Y 1.35 | EC | 2.68 H 5 | B+ | TOT | 749. | 6 | 84. | 19 |
| 77 | KR 1.30 | EC | 74.4 M 6 | B+ | TOT | 760. | 14 | 80. | 4 |
| 68 | CA 1.58 | EC | 67.629 M 2 | B+ | TOT | 829.9 | 6 | 89.1 | 5 |
| 68 | GA 1.57 | EC | 67.629 M 2 | B+ | | 836.0 | 6 | 88.0 | 4 |
| 89 | NB 1.36 | EC | 1.18 H 2 | B+ | | 986. | 21 | 65. | 6 |
| 85 | Y 1.22 | EC | 4.86 H 13 | B+ | TOT | 987. | 5 | 58. | 5 |
| 89 | NB 1.36 | EC | 1.18 H 2 | B+ | | 986. | 21 | 65. | 6 |
| 85 | Y 1.22 | EC | 4.86 H 13 | B+ | TOT | 987. | 5 | 58. | 5 |

TABLE 3-continued

| A | ELEMENT | Decay Mode | Half-Life | Rad. Type | | Radiation Energy (keV) | | Radiation Intensity (%) | |
|---|---------|------------|-----------|-----------|-----|------|----|--------|----|
| 89 | NB | EC | 1.18 H 2 | B+ | TOT | 1002. | 22 | 81. | 10 |
| | 1.73 | | | | | | | | |
| 85 | Y | EC | 4.86 H 13 | B+ | | 1008. | 5 | 52. | 4 |
| | 1.12 | | | | | | | | |
| 87 | ZR | EC | 1.68 H 1 | B+ | TOT | 1009. | 5 | 84.0 | 6 |
| | 1.81 | | | | | | | | |
| 110 | IN | EC | 69.1 M 5 | B+ | TOT | 1010. | 14 | 62. | 4 |
| | 1.33 | | | | | | | | |
| 87 | ZR | EC | 1.68 H 1 | B+ | | 1012. | 5 | 83.5 | 6 |
| | 1.80 | | | | | | | | |
| 110 | IN | EC | 69.1 M 5 | B+ | | 1015. | 14 | 61. | 4 |
| | 1.32 | | | | | | | | |
| 72 | AS | EC | 26.0 H 1 | B+ | | 1117.0 | 19 | 64.2 | 15 |
| | 1.80 | | | | | | | | |
| 110 | IN | EC | 69.1 M 5 | B+ | | 1015. | 14 | 61. | 4 |
| | 1.32 | | | | | | | | |
| 72 | AS | EC | 26.0 H 1 | B+ | | 1117.0 | 19 | 64.2 | 15 |
| | 1.53 | | | | | | | | |
| 72 | AS | EC | 26.0 H 1 | B+ | TOT | 1167.8 | 20 | 87.8 | 23 |
| | 2.18 | | | | | | | | |
| 76 | BR | EC | 16.2 H 2 | B+ | TOT | 1180. | 11 | 55. | 3 |
| | 1.38 | | | | | | | | |
| 89 | NB | EC | 1.9 H 2 | B+ | TOT | 1447. | 10 | 75. | 15 |
| | 2.32 | | | | | | | | |
| 89 | NB | EC | 1.9 H 2 | B+ | | 1462. | 9 | 74. | 15 |
| | 2.30 | | | | | | | | |
| 148 | TB | EC | 60 M 1 | B+ | TOT | 1558. | 20 | 51.38 | |
| | 1.71 | | | | | | | | |
| 120 | I | EC | 81.0 M 6 | B+ | TOT | 1657. | 99 | 78.34 | |
| | 2.76 | | | | | | | | |
| 148 | TB | EC | 60 M 1 | B+ | TOT | 1558. | 20 | 51.38 | |
| | 1.71 | | | | | | | | |
| 120 | I | EC | 81.0 M 6 | B+ | TOT | 1657. | 99 | 78.34 | |
| | 2.76 | | | | | | | | |
| 66 | GA | EC | 9.49 H 7 | B+ | TOT | 1736.6 | 20 | 56.1 | 15 |
| | 2.07 | | | | | | | | |
| 72 | GA | B– | 14.10 H 1 | B– | TOT | 501.6 | 15 | 100.2 | 12 |
| | 1.07 | | | | | | | | |
| 127 | SN | B– | 2.10 H 4 | B– | TOT | 511. | 74 | 103. | 10 |
| | 1.12 | | | | | | | | |
| 129 | TE | B– | 69.6 M 2 | B– | TOT | 520.2 | 19 | 99. | 12 |
| | 1.10 | | | | | | | | |
| 122 | SB | B– | 2.7238 D 2 | B– | | 521.2 | 10 | 66.73 | 20 |
| | 0.741 | | | | | | | | |
| 140 | LA | B– | 1.6781 D 7 | B– | TOT | 524.5 | 10 | 97.3 | 25 |
| | 1.09 | | | | | | | | |
| 71 | ZN | B– | 3.96 H 5 | B– | TOT | 540. | 6 | 99. | 3 |
| | 0.741 | | | | | | | | |
| 140 | LA | B– | 1.6781 D 7 | B– | TOT | 524.5 | 10 | 97.3 | 25 |
| | 1.09 | | | | | | | | |
| 71 | ZN | B– | 3.96 H 5 | B– | TOT | 540. | 6 | 99. | 3 |
| | 1.14 | | | | | | | | |
| 129 | TE | B– | 69.6 M 2 | B– | | 544.5 | 18 | 88. | 12 |
| | 1.02 | | | | | | | | |
| 24 | NA | B– | 14.9590 H | B– | | 554.1 | 3 | 99.944 | 4 |
| | 1.18 | | | | | | | | |
| 71 | ZN | B– | 3.96 H 5 | B– | | 573. | 5 | 89. | 3 |
| | 1.09 | | | | | | | | |
| 122 | SB | B– | 2.7238 D 2 | B– | TOT | 574.4 | 11 | 97.4 | 6 |
| | 1.19 | | | | | | | | |
| 31 | SI | B– | 157.3 M 3 | B– | | 595.6 | 4 | 99.93 | |
| | 1.27 | | | | | | | | |
| 190 | RE | B– | 3.2 H 2 | B– | TOT | 621. | 95 | 53. | 5 |
| | 0.703 | | | | | | | | |
| 31 | SI | B– | 157.3 M 3 | B– | | 595.6 | 4 | 99.93 | |
| | 1.27 | | | | | | | | |
| 190 | RE | B– | 3.2 H 2 | B– | TOT | 621. | 95 | 53. | 5 |
| | 0.703 | | | | | | | | |
| 65 | NI | B– | 2.51719 H | B– | TOT | 627.7 | 8 | 100.0 | 4 |
| | 1.34 | | | | | | | | |
| 77 | GE | B– | 11.30 H 1 | B– | TOT | 641.8 | 13 | 100.1 | 21 |
| | 1.37 | | | | | | | | |
| 91 | SR | B– | 9.63 H 5 | B– | TOT | 646.6 | 23 | 99. | 6 |
| | 1.37 | | | | | | | | |

TABLE 3-continued

| A | ELEMENT | Decay Mode | Half-Life | Rad. Type | | Radiation Energy (keV) | | Radiation Intensity (%) | |
|---|---|---|---|---|---|---|---|---|---|
| 166 | HO | B− | 26.80 H 2 | B− | TOT | 665.1 | 6 | 100. | 3 |
| | 1.42 | | | | | | | | |
| 145 | PR | B− | 5.984 H 10 | B− | TOT | 675. | 3 | 97.3 | 21 |
| | 1.40 | | | | | | | | |
| 152 | EU | B− | 9.274 H 9 | B− | TOT | 676.9 | 9 | 73. | 4 |
| | 1.05 | | | | | | | | |
| 145 | PR | B− | 5.984 H 10 | B− | | 683. | 3 | 95.0 | 20 |
| | 1.40 | | | | | | | | |
| 152 | EU | B− | 9.274 H 9 | B− | TOT | 676.9 | 9 | 73. | 4 |
| | 1.05 | | | | | | | | |
| 145 | PR | B− | 5.984 H 10 | B− | | 683. | 3 | 95.0 | 20 |
| | 1.38 | | | | | | | | |
| 166 | HO | B− | 26.80 H 2 | B− | | 693.6 | 5 | 50.0 | 21 |
| | 0.739 | | | | | | | | |
| 152 | EU | B− | 9.274 H 9 | B− | | 705.4 | 8 | 68. | 4 |
| | 1.02 | | | | | | | | |
| 97 | ZR | B− | 16.91 H 5 | B− | TOT | 706.6 | 10 | 99.4 | 5 |
| | 1.50 | | | | | | | | |
| 150 | PM | B− | 2.68 H 2 | B− | TOT | 725. | 36 | 100. | 6 |
| | 1.55 | | | | | | | | |
| 97 | ZR | B− | 16.91 H 5 | B− | | 757.0 | 9 | 87.8 | 3 |
| | 1.42 | | | | | | | | |
| 113 | AG | B− | 5.37 H 5 | B− | TOT | 757. | 10 | 100.4 | |
| | 1.62 | | | | | | | | |
| 97 | ZR | B− | 16.91 H 5 | B− | | 757.0 | 9 | 87.8 | 3 |
| | 1.42 | | | | | | | | |
| 113 | AG | B− | 5.37 H 5 | B− | TOT | 757. | 10 | 100.4 | |
| | 1.62 | | | | | | | | |
| 188 | RE | B− | 16.98 H 2 | B− | TOT | 763.81 | 19 | 100.0 | 21 |
| | 1.63 | | | | | | | | |
| 212 | BI | B− | 60.55 M 6 | B− | TOT | 769.6 | 19 | 64.06 | 14 |
| | 1.05 | | | | | | | | |
| 113 | AG | B− | 5.37 H 5 | B− | | 791. | 10 | 85.00 | |
| | 1.43 | | | | | | | | |
| 188 | RE | B− | 16.98 H 2 | B− | | 795.30 | 18 | 70.6 | 15 |
| | 1.20 | | | | | | | | |
| 194 | IR | B− | 19.15 H 3 | B− | TOT | 806.8 | 9 | 100.0 | 25 |
| | 1.72 | | | | | | | | |
| 142 | PR | B− | 19.12 H 5 | B− | TOT | 809.1 | 12 | 100.0 | 7 |
| | 1.72 | | | | | | | | |
| 56 | MN | B− | 2.5785 H 6 | B− | TOT | 829.9 | 7 | 100.1 | 14 |
| | 1.72 | | | | | | | | |
| 142 | PR | B− | 19.12 H 5 | B− | TOT | 809.1 | 12 | 100.0 | 7 |
| | 1.72 | | | | | | | | |
| 56 | MN | B− | 2.5785 H 6 | B− | TOT | 829.9 | 7 | 100.1 | 14 |
| | 1.77 | | | | | | | | |
| 212 | BI | B− | 60.55 M 6 | B− | | 832.5 | 17 | 55.46 | 10 |
| | 0.983 | | | | | | | | |
| 142 | PR | B− | 19.12 H 5 | B− | | 833.4 | 11 | 96.3 | 5 |
| | 1.71 | | | | | | | | |
| 194 | IR | B− | 19.15 H 3 | B− | | 846.4 | 8 | 85.4 | 20 |
| | 1.54 | | | | | | | | |
| 142 | LA | B− | 91.1 M 5 | B− | TOT | 872. | 4 | 99.4 | 10 |
| | 1.85 | | | | | | | | |
| 65 | NI | B− | 2.51719 H | B− | | 875.4 | 6 | 60.0 | 3 |
| | 1.12 | | | | | | | | |
| 139 | BA | B− | 83.06 M 28 | B− | TOT | 889.6 | 19 | 100.0 | 5 |
| | 1.89 | | | | | | | | |
| 65 | NI | B− | 2.51719 H | B− | | 875.4 | 6 | 60.0 | 3 |
| | 1.12 | | | | | | | | |
| 139 | BA | B− | 83.06 M 28 | B− | TOT | 889.6 | 19 | 100.0 | 5 |
| | 1.89 | | | | | | | | |
| 139 | BA | B− | 83.06 M 28 | B− | | 913.9 | 19 | 70.0 | 4 |
| | 1.36 | | | | | | | | |
| 90 | Y | B− | 64.10 H 8 | B− | | 933.7 | 12 | 99.9885 | 14 |
| | 1.99 | | | | | | | | |
| 141 | LA | B− | 3.92 H 3 | B− | TOT | 962. | 12 | 100.02 | 22 |
| | 2.05 | | | | | | | | |
| 141 | LA | B− | 3.92 H 3 | B− | | 974. | 12 | 98.14 | 7 |
| | 2.04 | | | | | | | | |
| 76 | AS | B− | 1.0778 D 2 | B− | TOT | 1070.0 | 11 | 100. | 3 |
| | 2.27 | | | | | | | | |
| 93 | Y | B− | 10.18 M 8 | B− | TOT | 1167. | 7 | 100.0 | 18 |
| | 2.49 | | | | | | | | |

TABLE 3-continued

| A | ELEMENT | Decay Mode | Half-Life | Rad. Type | | Radiation Energy (keV) | | Radiation Intensity (%) | |
|---|---------|------------|-----------|-----------|---|------------------------|---|-------------------------|---|
| 93 | Y 2.27 | B– | 10.18 H 8 | B– | | 1211. | 6 | 89.6 | 15 |
| 93 | Y 2.49 | B– | 10.18 H 8 | B– | TOT | 1167. | 7 | 100.0 | 18 |
| 93 | Y 2.31 | B– | 10.18 H 8 | B– | | 1211. | 6 | 89.6 | 15 |
| 56 | MN 1.46 | B– | 2.5785 H 6 | B– | | 1216.9 | 5 | 56.3 | 10 |
| 78 | AS 2.68 | B– | 90.7 M 2 | B– | TOT | 1244. | 7 | 101. | 9 |
| 76 | AS 1.38 | B– | 1.0778 D 2 | B– | | 1266.9 | 9 | 51.0 | 20 |
| 87 | KR 2.83 | B– | 76.3 M 6 | B– | TOT | 1333. | 3 | 100. | 4 |
| 112 | AG 3.02 | B– | 3.130 H 9 | B– | TOT | 1354. | 17 | 105. | 6 |
| 42 | K 3.05 | B– | 12.360 H 3 | B– | TOT | 1430.4 | 7 | 100.00 | 13 |
| 92 | Y 3.06 | B– | 3.54 H 1 | B– | TOT | 1436. | 6 | 100.1 | 21 |
| 92 | Y 2.83 | B– | 3.54 H 1 | B– | | 1553. | 5 | 85.7 | 16 |
| 42 | K 2.73 | B– | 12.360 H 3 | B– | | 1565.8 | 6 | 81.90 | 9 |
| 112 | AG 1.94 | B– | 3.130 H 9 | B– | | 1688. | 14 | 54. | 5 |

TABLE 4

| A | ELEMENT | Decay Mode | Half-Life | Rad. Type | | Radiation Energy (keV) | | Radiation Intensity (%) | |
|---|---------|------------|-----------|-----------|---|------------------------|---|-------------------------|---|
| 125 | TE 0.0358 | IT | 57.40 D 15 | G | X KA1 | 27.47230 | 20 | 61.3 | 23 |
| 125 | I 0.0435 | EC | 59.402 D 1 | G | X KA1 | 27.47230 | 20 | 74.3 | 17 |
| 93 | MO 0.0537 | EC | 3.5E + 3 Y 7 | G | | 30.770 | 20 | 82. | 5 |
| 133 | BA 0.0428 | EC | 10.52 Y 13 | G | X KA1 | 30.9728 | 3 | 64.9 | 12 |
| 145 | SM 0.0591 | EC | 340 D 3 | G | X KA1 | 38.7247 | 5 | 71.6 | 12 |
| 147 | EU 0.0447 | EC | 24 D 1 | G | X KA1 | 40.1181 | 3 | 52. | 3 |
| 146 | GD 0.0455 | EC | 48.27 D 10 | G | X KA2 | 40.9019 | 3 | 52.2 | 8 |
| 146 | GD 0.0836 | EC | 48.27 D 10 | G | X KA1 | 41.5422 | 3 | 94.5 | 14 |
| 157 | TB 0.0455 | EC | 99 Y 10 | G | X KA2 | 42.3089 | 3 | 71. | 6 |
| 146 | GD 0.0836 | EC | 48.27 D 10 | G | X KA1 | 41.5422 | 3 | 94.5 | 14 |
| 157 | TB 0.0644 | EC | 99 Y 10 | G | X KA2 | 42.3089 | 3 | 71. | 6 |
| 254 | ES 0.0907 | A | 275.5 D 5 | G | | 42.60 | 10 | 100.0 | |
| 157 | TB 0.118 | EC | 99 Y 10 | G | X KA1 | 42.9962 | 3 | 129. | 10 |
| 242 | AM 0.103 | IT | 141 Y 2 | G | | 48.63 | 5 | 99.50 | 20 |
| 157 | TB 0.0528 | EC | 99 Y 10 | G | X KB | 48.70 | | 51. | 4 |
| 169 | YB 0.0562 | EC | 32.026 D 5 | G | X KA2 | 49.7726 | 4 | 53.0 | 10 |
| 186 | RE 0.0936 | IT | 2.0E + 5 Y 5 | G | | 50. | 37 | 88. | 3 |
| 169 | YB 0.0562 | EC | 32.026 D 5 | G | X KA2 | 49.7726 | 4 | 53.0 | 10 |
| 186 | RE 0.0936 | IT | 2.0E + 5 Y 5 | G | | 50. | 37 | 88. | 3 |

TABLE 4-continued

| A | ELEMENT | Decay Mode | Half-Life | Rad. Type | | Radiation Energy (keV) | | Radiation Intensity (%) | |
|---|---|---|---|---|---|---|---|---|---|
| 169 | YB 0.101 | EC | 32.026 D 5 | G | X KA1 | 50.7416 | 4 | 93.8 | 18 |
| 173 | LU 0.0862 | EC | 1.37 Y 1 | G | X KA1 | 52.3889 | 5 | 77.2 | 21 |
| 172 | HF 0.0734 | EC | 1.87 Y 3 | G | X KA1 | 54.0698 | 5 | 64. | 7 |
| 177 | LU 0.0690 | B– | 160.4 D 3 | G | X KA1 | 55.7902 | 8 | 58.0 | 11 |
| 179 | HF 0.0670 | IT | 25.05 D 25 | G | X KA1 | 55.7902 | 8 | 56.4 | 19 |
| 183 | RE 0.0757 | EC | 70.0 D 11 | G | X KA1 | 59.31820 | 10 | 59.9 | 20 |
| 44 | TI 0.0862 | EC | 49 Y 3 | G | | 67.88 | | 94.4 | 15 |
| 172 | HF 0.0734 | EC | 1.87 Y 3 | G | X KA1 | 54.0698 | 5 | 64. | 7 |
| 177 | LU 0.0690 | B– | 160.4 D 3 | G | X KA1 | 55.7902 | 8 | 58.0 | 11 |
| 179 | HF 0.0670 | IT | 25.05 D 25 | G | X KA1 | 55.7902 | 8 | 56.4 | 19 |
| 183 | RE 0.0757 | EC | 70.0 D 11 | G | X KA1 | 59.31820 | 10 | 59.9 | 20 |
| 44 | TI 0.136 | EC | 49 Y 3 | G | | 67.88 | | 94.4 | 15 |
| 243 | AM 0.108 | A | 7370 Y 15 | G | | 74.660 | 20 | 68.2 | 14 |
| 44 | TI 0.161 | EC | 49 Y 3 | G | | 78.34 | | 96.2 | 3 |
| 178 | HF 0.122 | IT | 31 Y 1 | G | | 88.862 | 6 | 64.4 | 14 |

References

1. Berger, M. J. and Seltzer, S. M. Stopping powers and ranges of electrons and positrons (2nd Ed.). U.S. Dept. Commerce Publication NBSIR 82-2550-A (1983)
2. Bottcher, H. D., Schopohl, B., Liermann, D., Kollath, J., and Adamietz, I. A. Endovascular irradiation-a new method to avoid recurrent stenosis after stent implantation in peripheral arteries: technique and preliminary results. Int. J. Rad. Onc. Biol. Phys. 29, 183–186 (1994)
3. Friedell, H. L., Thomas, C. I., and Krohmer, J. S. Description of an $Sr^{90}$ beta-ray applicator and its use on the eye. Amer. J. Roentq. 65, 232–245 (1951)
4. Gellman, J., Healey G., Qingsheng, C., Tselentakis, M. J. The effects of very low dose irradiation on restenosis following balloon angioplasty. A study in the atherosclerotic rabbit. Circulation 84, Supple 11, 46A–59A (1991)
5. Johns, H. E., and Cunningham, J. R. The Physics of Radiology (4th Edition). Charles Thomas, Publisher (Springfield, Ill., 1983).
6. Landau, C., Lange, R. A., Hillis, L. D. Percutaneous transluminal coronary angioplasty. NEJM 330, 981–993 (1994)
7. Mayberg, M. R., Luo, Z., London, S., Gajdusek, C., Rasey, J. S. Radiation inhibition of intimal hyperplasia after arterial injury. Rad. Res. 142,212–220 (1995)
8. MIRD. Method of calculation: 'S", absorbed dose per unit cumulated activity for selected radionuclides and organs. MIRD Pamphlet #11 (1975).
9. Nath, R., Anderson, L., Luxton, G., et. al. Dosimetry of interstitial brachytherapy sources: recommendations of the AAPM radiation therapy committee task group No. 43. Med. Phys. 22, 209–234 (1995)
10. Prestwich, W. V., Kennet, T. J., and Kus, F. W. The dose distribution produced by a $P^{32}$-coated stent. Med. Phys. 22, 313–320 (1995)
11. Schwartz, R. S., Koval, T. M., Edwards, W. D., Camrud, A. R., Bailey, K. R., Brown, K., Vlietstra, R. E., and Holmes, D. R. Effect of external beam irradiation on neointimal hyperplasia after experimental coronary artery injury. J. Am. Col. Cardiol. 19, 1106–1113 (1992).
12. Wiederman, J., Marobe, C., Amols, H., Schwartz, A., and Weinberger, J. Intracoronary irradiation markedly reduces restenosis after balloon angioplasty in a porcine model. J. Amer. Col. Card. 23, 1491-8 (1994)
13. Wiederman, J., Leavy, J., Amols, H., Schwartz, A., Homma, S., Marobe, C., and Weinberger, J. Effects of high dose intracoronary irradiation on vasomotor function and smooth muscle histopathology. Am. J. Phys. (Heart and Circ. Physiol.) 267, H125–H132 (1994)
14. Williamson, J. F., and Zuofend, L. Monte carlo aided dosimetry of the microselectron pulsed and high dose-rate $^{192}$Ir sources. Med. Phys. 22, 809–819 (1995)
15. Desai, N.P., & Hubbell, J.A. (1991). Biological responses to polyethylene oxide modified polyethylene terephthalate surfaces. Journal of Biomedical Materials Research, 25(7), 829–43.
16. Gombotz, W. R., Wang, G. H., Horbett, T. A., & Hoffman, A. S. (1991). Protein adsorption to poly (ethylene oxide) surfaces. Journal of Biomedical Materials Research, 25(12), 1547–62.
17. Massia, S. P., & Hubbell, J. A. (1991). Human endothelial cell interactions with surface-coupled adhesion peptides on a nonadhesive glass substrate and two polymeric biomaterials. Journal of Biomedical Matereials Research, 25(2), 223–42.
18. Afshan, A., Jehangir, M., Ashraf, M., Waqar, A., & Chiotellis, E. (1994). Formulation of a single-component kit for the preparation of technetium-99 m labeled ethyl cysteinate dimer; biological and clinical evaluation. European Journal of Nuclear Medicine, 21(9), 991–5.

19. Hannant, D., Bowen, J. G., Price, M. R., & Baldwin, R. W. (1980). Radioiodination of rat hepatoma-specific antigens and retention of serological reactivity. *British Journal of Cancer*, 41(5), 716–23.
20. Hartikka, M., Vihko, P., Sodervall, M., Hakalahti, L., Torniainen, P., & Vihko, R. (1989). Radio labeling of monoclonal antibodies: optimization of conjugation of DTPA to F(ab')2-fragments and a novel measurement of the degree of conjugation using Eu(III)-labeling. *European Journal of Nuclear Medicine*, 15(3), 157–61.
21. Ingvar, M., Eriksson, L., Rogers, G. A., Stone, E. S., & Widen, L. (1991). Rapid feasibility studies of tracers for positron emission tomography: high-resolution PET in small animals with kinetic analysis. *Journal of Cerebra Blood Flow & Metabolism*, 11(6), 926–31.
22. Portoles, P., Rojo, J. M., & Janeway, C. J. (1990). A simple method for the radioactive iodination of CD4 molecules. *Journal of Immunological Methods*, 129(1), 105–9.
23. Samuel, D., Amlot, P. L., & Abuknesha, R. A. (1985). A new method of iodinating ovalbumin, a protein which lacks accessible tyrosine groups, by conjugation to a highly fluorescent coumarin active ester, CASE. *Journal of Immunological Methods*, 81(1), 123–30.
24. Wafelman, A. R., Konings, M. C., Hoefnagel, C. A., Maes, R. A., & Beijnen, J. H. (1994). Synthesis, radiolabelling and stability of radioiodinated miodobenzylguanidine, a review. *Applied Radiation & Isotopes*, 45(10), 997–107
25. Polymers FAQ, Polymers archive on the Internet complied by Jim Coffey, Aug. 11, 1995.

What is claimed is:

1. An apparatus for reducing restenosis after arterial intervention in a patient's artery comprising:

a balloon catheter with a fluid delivery port connected thereto; and a radioactive fluid inserted into the balloon catheter through the fluid delivery port, said radioactive fluid being selected from the group consisting of non-iodine and non-phosphorus based radioisotopes that decay with emission of beta plus or beta minus radiation, that have a half-life of between approximately 1 and 72 hours, that have an average decay energy of approximately 500–2000 keV, and that have radiation intensity of greater than or equal to approximately 50%, said radiation intensity being measured in % per decay.

2. The apparatus of claim 1, wherein said non-iodine and non-phosphorus based radioisotopes that decay with emission of beta plus or beta minus radiation, that have a half-life of between approximately 1 and 72 hours, that have an average decay energy of approximately 500–2000 keV, and that have radiation intensity of greater than or equal to approximately 50%, said radiation intensity being measured in % per decay, are selected from the group consisting of NA-24, SI-31, K-42, SC-43, SC-44, CO-55, MN-56, CU-61, NI-65, GA-66, GA-68, ZN-71, GA-72, AS-72, SE-73, BR-75, AS-76, BR-76, GE-77, KR-77, AS-78, Y-85, KR-87, ZR-87, NB-89, Y-90, NB-90, SR-91, Y-92, Y-93, ZR-97, IN-110, AG-112, AG-113, SB-122, SN-127, TE-129, BA-139, LA-140, LA-141, LA-142, PR-142, PR-145, TB-148, PM-150, EU-152, HO-166, RE-188, RE-190, IR-194, BI-212, and radioactive sodium-chloride.

3. The apparatus of claim 2, wherein said non-iodine and non-phosphorus based radioisotopes that decay with emission of beta plus or beta minus radiation, that have a half-life of between approximately 1 and 72 hours, that have an average decay energy of approximately 500–2000 keV, and that have radiation intensity of greater than or equal to approximately 50%, said radiation intensity being measured in % per decay, are dissolved in an aqueous fluid.

4. The apparatus of claim 2, wherein said non-iodine and non-phosphorus based radioisotopes that decay with emission of beta plus or beta minus radiation, that have a half-life of between approximately 1 and 72 hours, that have an average decay energy of approximately 500–2000 keV, and that have radiation intensity of greater than or equal to approximately 50%, said radiation intensity being measured in % per decay, are in gas phase.

5. A method for reducing restenosis after arterial intervention in a patient's artery comprising:

inserting a balloon catheter with a fluid delivery port connected thereto into the patient's artery;

providing a radioactive fluid selected from the group consisting of non-iodine and nonphosphorus based radioisotopes that decay with emission of beta plus or beta minus radiation, that have a half-life of between approximately 1 and 72 hours, that have an average decay energy of approximately 500–2000 KeV, and that have radiation intensity of greater than or equal to approximately 50%, said radiation intensity being measured in % per decay; and inserting the radioactive fluid into the balloon catheter through the fluid delivery port.

6. The method of claim 5, wherein said non-iodine and non-phosphorus based radioisotopes that decay with emission of beta plus or beta minus radiation, that have a half-life of between approximately 1 and 72 hours, that have an average decay energy of approximately 500–2000 keV, and that have radiation intensity of greater than or equal to approximately 50%, said radiation intensity being measured in % per decay, are selected from the group consisting of NA-24, SI-31, K-42, SC-43, SC-44, CO-55, MN-56, CU-61, NI-65, GA-66, GA-68, ZN-71, GA-72, AS-72, SE-73, BR-75, AS-76, BR-76, GE-77, KR-77, AS-78, Y-85, KR-87, ZR-87, NB-89, Y-90, NB-90, SR-91, Y-92, Y-93, ZR-97, IN-110, AG-112, AG-113, SB-122, SN-127, TE-129, BA-139, LA-140, LA-141, LA-142, PR-142, PR-145, TB-148, PM-150, EU-152, HO-166, RE-188, RE-190, IR-194, BI-212, and radioactive sodium-chloride.

7. The method of claim 6, wherein said non-iodine and non-phosphorus based radioisotopes that decay with emission of beta plus or beta minus radiation, that have a half-life of between approximately 1 and 72 hours, that have an average decay energy of approximately 500–2000 keV, and that have radiation intensity of greater than or equal to approximately 50%, said radiation intensity being measured in % per decay, are dissolved in an aqueous fluid.

8. The method of claim 6, wherein said non-iodine and non-phosphorus based radioisotopes that decay with emission of beta plus or beta minus radiation, that have a half-life of between approximately 1 and 72 hours, that have an average decay energy of approximately 500–2000 keV, and that have radiation intensity of greater than or equal to approximately 50%, said radiation intensity being measured in % per decay, are in gas phase.

9. A method for reducing restenosis after arterial intervention in a patient's artery comprising:

inserting a balloon catheter with a fluid delivery port connected thereto into the patient's artery; and selecting a radioactive fluid from the group consisting of non-iodine and nonphosphorus based radioisotopes that decay with emission of beta plus or beta minus radiation, that have a half-life of between approximately 1 and 72 hours, that have an average decay energy of approximately 500–2000 KeV, and that have radiation intensity of greater than or equal to approximately 50%, said radiation intensity being measured in % per decay; and inserting the radioactive fluid into the balloon catheter through the fluid delivery port.

* * * * *